United States Patent [19]

Koyama et al.

[11] 4,055,428
[45] Oct. 25, 1977

[54] REDOX DYE RELEASERS O-SULFONAMIDOPHENOL

[75] Inventors: Kōichi Koyama; Yukio Maekawa; Masami Miyakawa, all of Minami-ashigara, Japan

[73] Assignee: Fuji Photo Film Co., Ltd., Minami-ashigara, Japan

[21] Appl. No.: 670,763

[22] Filed: Mar. 26, 1976

[30] Foreign Application Priority Data

Mar. 28, 1975 Japan .................................. 50-38305

[51] Int. Cl.² .................. G03C 1/40; G03C 7/00; G03C 1/76; G03C 1/10
[52] U.S. Cl. ................................. 96/73; 96/3; 96/29 D; 96/74; 96/77; 96/99; 96/100 R
[58] Field of Search ..................... 96/3, 29 D, 73, 77, 96/74, 99, 100, 56.6

[56] References Cited

U.S. PATENT DOCUMENTS

| 2,306,410 | 12/1942 | Schinzel | 96/100 |
| 3,227,550 | 1/1966 | Whitmore et al. | 96/77 |
| 3,751,406 | 8/1973 | Bloom | 96/29 D |
| B 351,673 | 1/1975 | Fleckenstein et al. | 96/77 |

FOREIGN PATENT DOCUMENTS

512,559  9/1939  United Kingdom

OTHER PUBLICATIONS

"Photographic Systems", *Research Disclosure* No. 13024, Feb. 1975.

*Primary Examiner*—David Klein
*Assistant Examiner*—Richard L. Schilling
*Attorney, Agent, or Firm*—Sughrue, Rothwell, Mion, Zinn and Macpeak

[57] ABSTRACT

A color photographic material for, in particular, a color diffusion transfer process having at least one silver halide emulsion layer having associated therewith a dye releasing redox compound shown by the formula

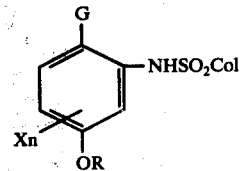

wherein G represents a hydroxyl group or a group yielding a hydroxyl group by hydrolysis, Col represents a dye or a group yielding a dye by hydrolysis, R represents an alkyl group or an aromatic group, X represents a substituent comprising an electron donating group or substituents, which may be same or different, at least one of which comprises an electron donating group, and n is 1, 2, or 3; where X moieties may form a condensed ring (excluding an aromatic hydrocarbon ring) with each other or with OR, wherein the total carbon number of $X_n$ and R is more than 8.

28 Claims, No Drawings

REDOX DYE RELEASERS O-SULFONAMIDOPHENOL

BACKGROUND OF THE INVENTION

1. Field of the Invention

The present invention relates to color photographic materials, more particularly, it relates to color photographic materials containing compounds that release a diffusible dye by a redox reaction associated with the development of silver halide.

2. Description of the Prior Art

A color diffusion transfer dye image forming process using dye releasing redox compounds is disclosed in Japanese Patent Application (OPI) 33,826/1973. The dye releasing redox compounds described in that patent application are p-sulfonamidophenol compounds or p-sulfonamidonaphthol compounds, the dye moiety of which has bonded thereto a non-diffusible phenol moiety or naphthol moiety at the p-position thereof through a sulfonamide group. When a diffusion transfer color photographic unit containing such a dye releasing redox compound in the photosensitive element is image-wise exposed and developed in the presence of a photosensitive silver halide emulsion, the redox compound is oxidized in proportion to the amount of the developed silver halide, the oxidized redox compound is decomposed into a dye moiety having a sulfonamide group and a non-diffusible benzoquinone or non-diffusible naphthoquinone by the action of an alkaline processing solution, and the dye moiety is transferred into an image receiving element of the unit to provide a transfer dye image.

However, according to our experiments and investigations, it was confirmed that the aforesaid p-sulfonamidophenol redox compound did not give a sufficient transfer dye image density, and, in the case of using the p-sulfonamidonaphthol redox compound, non-diffusible naphthoquinone remained in the photosensitive layer after dye release to form a yellow stain therein, and, hence, in the latter case while the transfer image might be utilized the photosensitive element having such a photosensitive layer could not be used as a negative or positive image even if the photosensitive element was subjected to silver bleaching.

SUMMARY OF THE INVENTION

It is therefore one object of this invention to provide color photographic materials containing novel dye releasing redox compounds.

It is another object of this invention to provide color photographic materials containing dye releasing redox compounds capable of giving a high density transfer image when used for a diffusion transfer system.

It is still another object of this invention to provide color photographic materials containing dye releasing redox compounds which give dye images having less residual color or yellow stain after dye release.

Other objects of this invention will be apparent from the following descriptions of this specification.

The inventors have discovered that the above objects of this invention can be attained by color photographic materials containing a compound represented by the following general formula as a dye releasing redox compound;

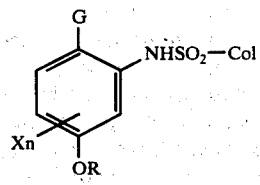

wherein G represents a hydroxyl group or a group which yields a hydroxyl group by hydrolysis, Col represents a dye or a group which yields a dye by hydrolysis, R represents an alkyl group or an aromatic group, X represents an electron donating group when $n$ is 1, or substituents, which may be the same or different, that is, at least one of the substituents X comprising an electron donating group, when $n$ is 2 or 3, and $n$ represents 1, 2, or 3, where X moieties may form a condensed ring (excluding an aromatic hydrocarbon ring with each other or between X and OR, and wherein the total carbon number of X$n$ and R is greater than 8.

Thus, according to the present invention, there are provided color photographic materials containing dye releasing redox compounds represented by the above described general formula.

DESCRIPTION OF THE PREFERRED EMBODIMENTS

In the dye releasing redox compounds of this invention shown by the above general formula, specific examples of G include a hydroxyl group and an acyloxy group such as, for example, an acetoxy group, a benzoyloxy group, a p-nitrobenzoyloxy group, a methanesulfonyloxy group, a p-toluenesulfonyloxy group, a propionyloxy group, in general, a group which yields a hydroxyl group by hydrolysis with alkali in a photographic processing solution. Examples of Col include groups drived from an azo dye, an azomethine dye, an indoaniline dye, an indophenol dye, a triphenylmethane dye, an anthraquinone dye, an indigo dye, and the metal complex salts of these dyes as well as the groups yielding these group by hydrolysis, such as the acylated auxochromes of dyes as described in, for instance, Japanese Patent Application (OPI) No. 125,818/1973 and in U.S. Pat. Nos. 3,222,196 and 3,307,947 and in Senryo Binran (Dye Handbook) published by Maruzen. The latter case, that is, the dye image forming material of the general formula described above in which Col represents the acylated auxochrome, is particularly useful for temporarily shifting the absorption of the dye to a shorter wave length side during exposure for the purpose of preventing desensitization based on light absorption occuring when coating the dye image forming material together with a photosensitive silver halide emulsion. In addition, for this purpose, a dye can be utilized where the color thereof differs when the dye is transferred into a mordant layer as compared to when the dye is present in a silver halide emulsion layer. Furthermore, the dye or group represented by Col may have a group capable of providing water solubility, i.e., a group capable of being released such as a hydroxyl group, a sulfonic acid or salts thereof, a sulfonamido group, a carboxy group, and the like; of these groups, a carboxy group and a sulfonamide group are particularly preferred.

Preferred examples of R include a straight chain or branched chain alkyl group having 1 to 24 carbon atoms (e.g., a methyl group, ethyl group, propyl group, butyl group, pentyl group, hexyl group, octyl group, dodecyl group, pentadecyl group, hexadecyl group, octadecyl group, isopropyl group, isobutyl group, t-butyl group, t-amyl group, neopentyl group, etc.,), a substituted alkyl group (such as an acylaminomethyl, dimethylethyl, diethylaminoethyl, hydroxyethyl, hydroxymethyl, methoxymethyl, methoxyethyl benzyl group, etc., preferably a hydroxyethyl or methoxyethyl group,), a phenyl group, and a substituted phenyl group (such as an o, m, or p-acylaminophenol, nitrophenyl, p-amylaminophenyl, alkoxyphenyl group, and the like, preferably, p-acetylaminophenyl or p-methoxyphenyl.

Preferred examples of X when $n=1$ are a straight or branched chain alkyl group (e.g., a methyl, ethyl, propyl, butyl, pentyl, hexyl, octyl, dodecyl, pentadecyl, hexadecyl, octadecyl, isopropyl t-butyl, etc., group) a straight or branched chain alkoxy group (e.g., methoxy, ethoxy propoxy, butoxy, hexyloxy, octoxy, dodecyloxy, pentadecyloxy, hexadecyloxy, isopropoxy, t-butoxy, etc., group), an alkylthio group, an arylthio group, and an acylamino group, and, when $n$ is 2 or 3, the X groups may be different from each other such as a halogen atom (e.g., chlorine, bromine, etc.), an alkyl group or an alkoxy group as defined above, an acylamino group, a nitro group, a cyano group, an alkylthio group, an arylthio group and the like, but at least one of them must be an electron donating group such as an alkyl group, an alkyloxy group, an alkylthio group, and an arylthio group. It is preferred for each of the recited groups for X which can contain carbon atoms that they contain up to 24 carbon atoms, with the proviso that when $n$ is 1 X most preferably has more than 8 carbon atoms, and when $n$ is 2 or 3 most preferably at least one of the groups for X has more than 8 carbon atoms and the other group(s) comprises 1 to 10 carbon atoms. The X groups may form a condensed ring with each other (when $n$ is 2 or 3) or together with OR; examples of such condensed rings will become apparent from the examples of the dye releasing redox compounds of this invention latter illustrated in this specification. In addition, an aromatic hydrocarbon condensed ring is undesirable as such a condensed ring of X groups since it forms color stains in portions where the redox compound remains.

The dye releasing redox compound used in this invention requires a ballast group to render it non-diffusible to prevent the compound from being diffused away as it is by an alkaline aqueous solution used for the development of the color photographic material. The size or the carbon number of the group required for such a ballast group depends upon the development conditions such as the processing time and the concentration of the alkali as well as the number and kinds of the water-solubilizing groups of the Col moiety, but it is required that the total carbon number of X and R in the redox compound be greater than 8. If the total carbon number becomes larger, the use of the redox compound is sometimes disadvantageous in solubility and extinction coefficient, but, in principle, there is no upper limit on the total carbon number. In general, howevern it is most preferred that the total carbon number of X and R be in the range of from 13 to 25.

"Research Disclosure", No. 13024, (1975) discloses o-sulfonamidophenols and shows that of these sulfonamidophenols 2-sulfonamidophenols having an alkyl group at the 5-position scarcely show any development activity, and, hence, do not release a dye. Thus, it is clear that the compound of this invention having an OR group at the 4-position of the phenol group thereof has important differences from known 2-sulfonamidophenols. The compound of this invention forms an o-quinoneimide by a redox reaction at development and the product releases the sulfonamido moiety by the action of hydrolysis. It is believed that the o-benzoquinone formed from the released moiety only shows a hypsochromic absorption as compared with the aforesaid known naphthoquinones, i.e., does not cause residual color to arise, and this contributes to reduce the formation of the residual color in a photosensitive layer by the compound after dye releasing.

The dye releasing type redox compounds used in this invention are illustrated below, but it should be understood that the redox compounds used in this invention are not limited to these compounds.

Compound 1

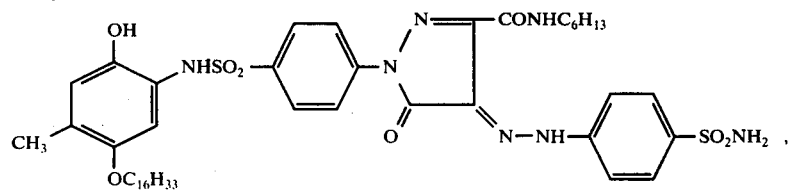

Compound 2

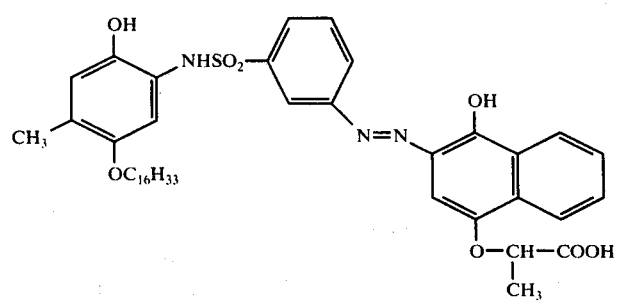

Compound 3

-continued
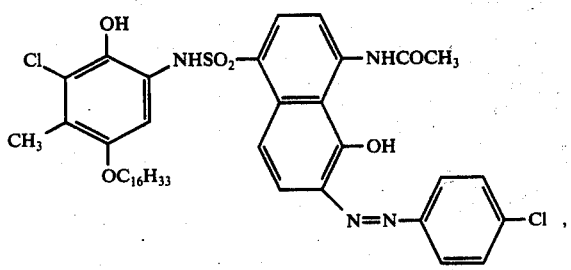
Compound 4
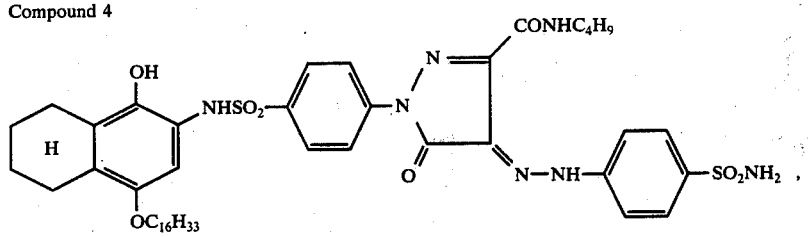
Compound 5
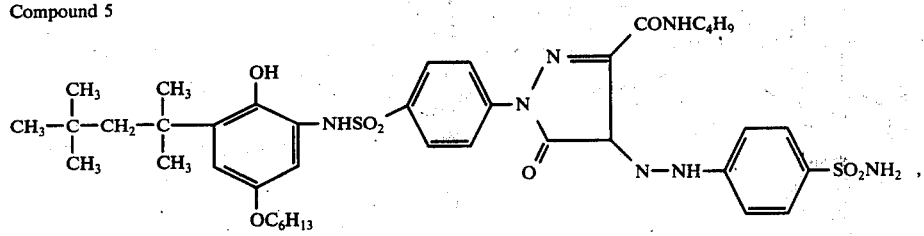
Compound 6
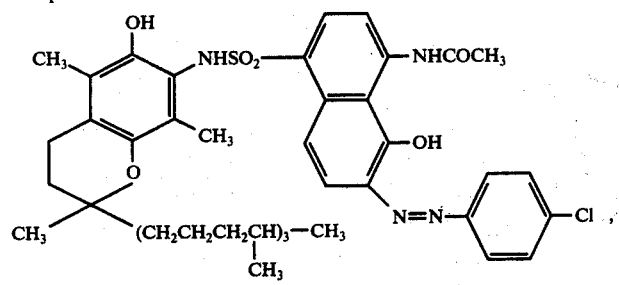
Compound 7
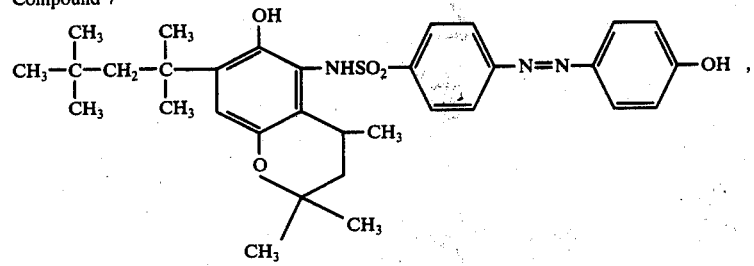
Compound 8
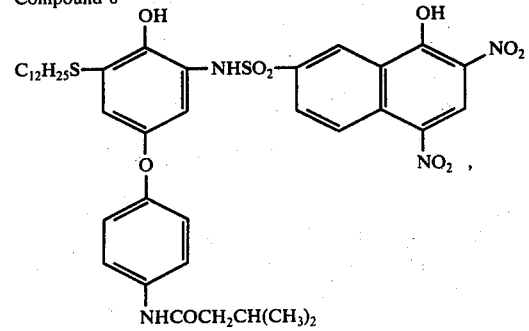
Compound 9

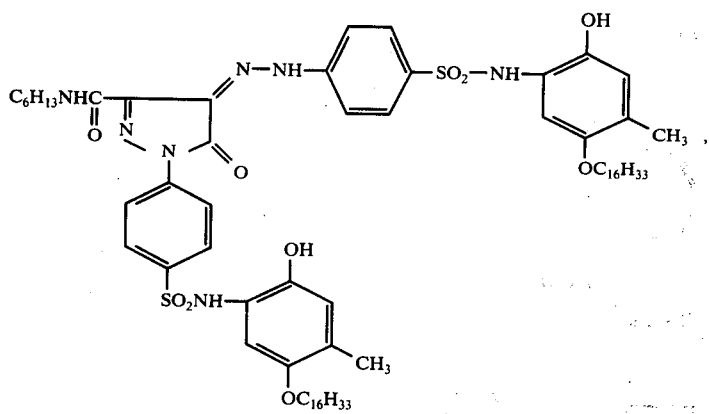
Compound 10
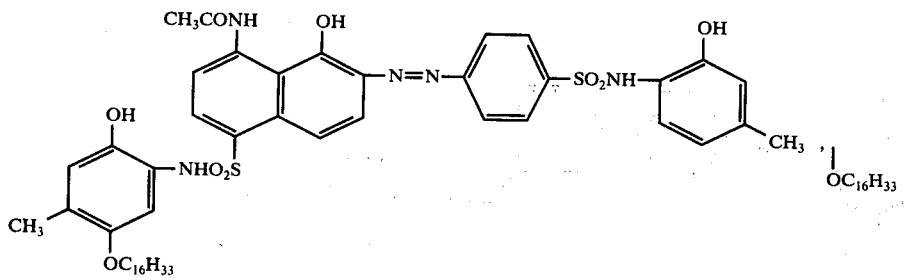
Compound 11
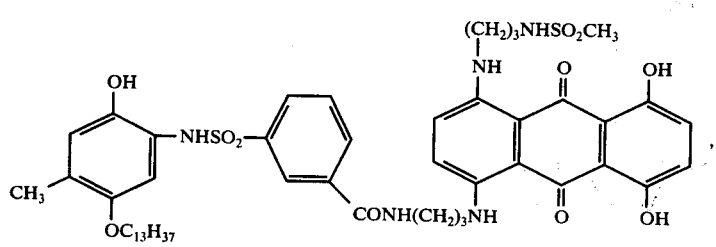
Compound 12
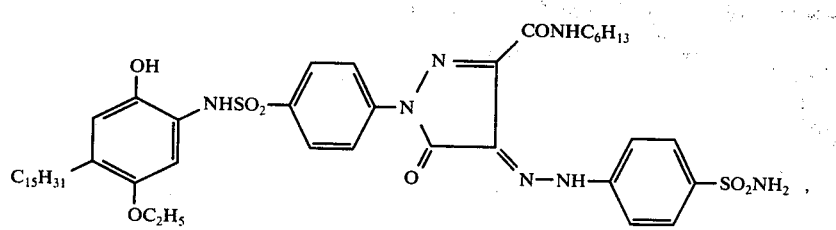
Compound 13
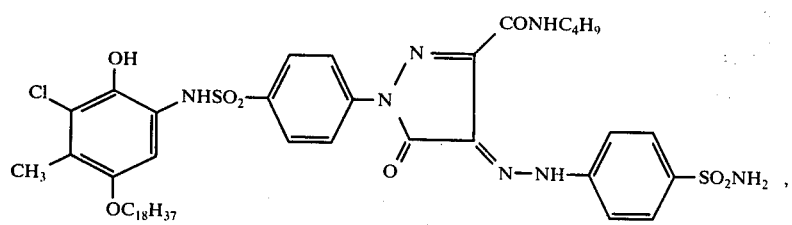
Compound 14

-continued
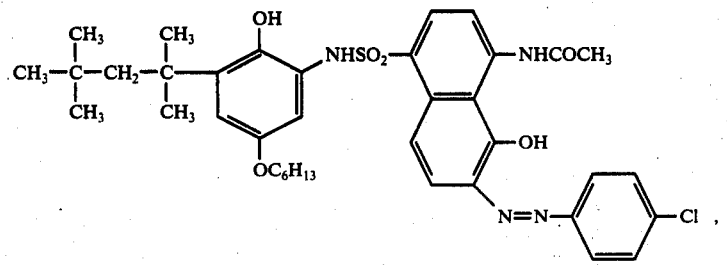
Compound 15
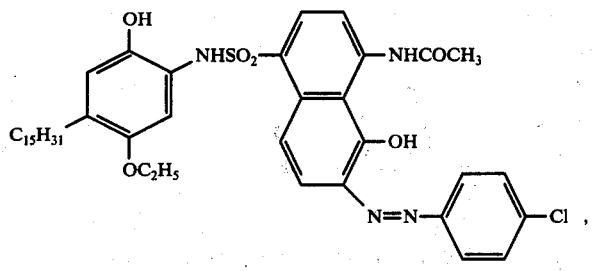
Compound 16
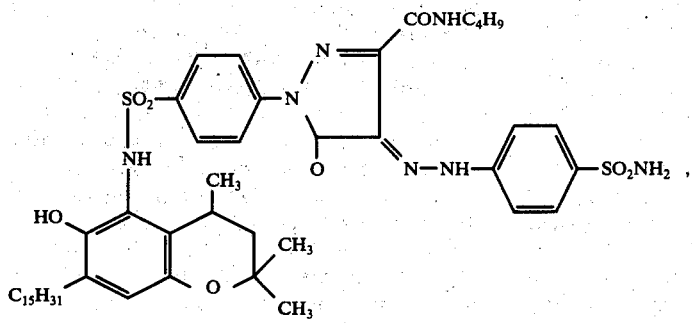
Compound 17
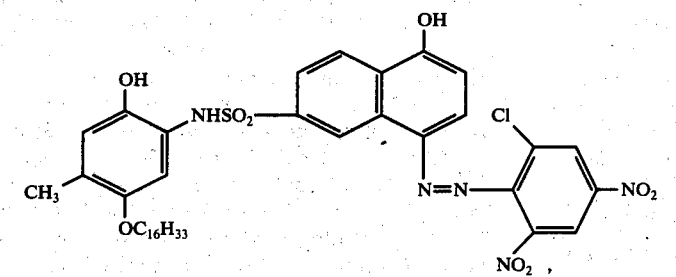
Compound 18
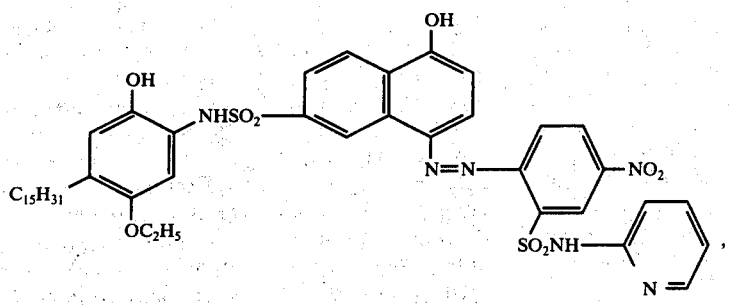
Compound 19

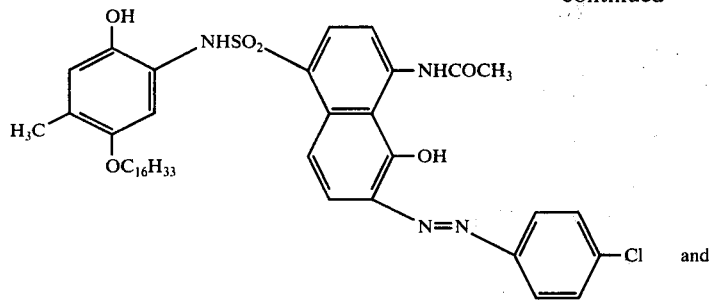

and

Compound 20

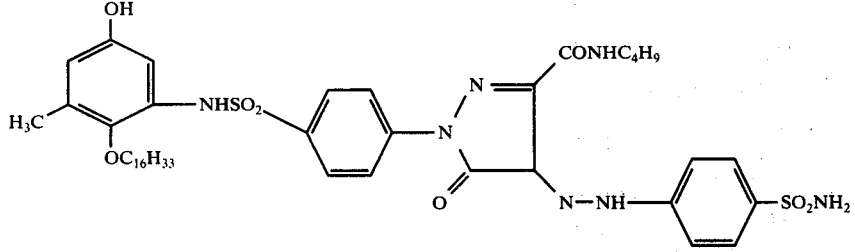

The compound of this invention is incorporated in a color photographic material in associated relationship with a photosensitive silver halide emulsion layer. When the color photographic material containing the dye releasing redox compound of this invention is processed in an alkaline aqueous processing solution after image wise exposure, the compound of this invention is oxidized at areas where the development of silver halide occurs and then releases a dye by hydrolysis; thus, by subjecting the color photographic material in which the dye has been transferred into an image-receiving element thereof or from which the dye has been washed off, to a bleach treatment and fix treatment, a color image can also be obtained, i.e., dyes diffused to the image receiving layer yield a positive image while the light-sensitive element can be bleached and fixed to yield a negative image.

When a conventional silver halide emulsion which undergoes development of silver halide in proportion to the amount of exposure is used, the transferred image provides a negative image and the residual image provides a positive image. On the other hand, when a direct reversal silver halide emulsion, a development inhibitor releasing (DIR) reversal silver halide emulsion as described in U.S. Pat. Nos. 3,277,551; 3,227,554; and 3,364,022, or a reversal silver halide emulsion using the solution physical development as described in British Pat. No. 904,364 is used, the transferred image forms a positive image and the residual image forms a negative image. Any of the negative image or positive images can be employed and further, if necessary, a combination of the negative image and the positive image can be also employed.

In the development of the color photographic material containing the dye releasing redox compound of this invention, to smooth the energy transfer which is comparatively unmovable between the color image forming material and silver halide grains, it is preferred to perform the development in the presence of an auxiliary developing agent, in this case, no primary developing agent being used. Examples of the auxiliary developing agent used for the purpose are given below:
1-phenyl-3-pyrazolidone,
1-phenyl-4,4-dimethyl-3-pyrazolidone,
1-phenyl-4-methyl-3-pyrazolidone,
p-aminophenol,
N-methyl-p-aminophenol,
N,N-diethylamino-phenol-p-tolylhydroquinone
N,N-diethyl-p-phenylenediamine, and
6-hydroxy-1,2,3,4-tetrahydroquinoline.

The dye releasing redox compound of this invention is generally dispersed in a carrier of a hydrophilic colloid in the following manner. That is, the dye releasing redox compound is dissolved in an organic solvent and the solution is dispersed as fine droplets in an aqueous solution of a hydrophilic colloid. When a solvent which is readily volatile, such as ethyl acetate, tetrahydrofuran, methyl ethyl ketone, etc., is used as the organic solvent for the redox compound, the solvent can be removed from the dispersion in a drying step for the photographic emulsion layers or by the method as described in U.S. Pat. Nos. 2,322,027 or 2,801,171, while when a solvent which is easily soluble in water, such as dimethyl formamide, 2-methoxy ethanol, etc., is used as the organic solvent, the solvent can be removed by the water washing method as described in U.S. Pat. Nos. 2,949,360 and 3,396,027. However, for stabilizing the dispersion of the dye releasing redox compound and promoting the progress of the dye image forming process, it is advantageous to use a solvent which is substantially insoluble in water and which has a boiling point higher than 200° C. at normal pressure. Examples of such solvent are, for instance, dibutyl phthalate, tricresyl phosphate, trihexyl phosphate, N,N-diethyl lauramide, etc. Furthermore, for promoting the dissolution of the dye releasing redox compound in the solvent, it is desired to use the above mentioned volatile or water soluble organic solvent as an auxiliary solvent together with the aforesaid high boiling point solvent.

Still further, in place of the high boiling solvent or together with the high boiling solvent, an oleophilic polymer can also be used. Examples of such oleophilic polymers are polyester resins prepared by the polycondensation of polyhydric alcohols and polybasic acids. Other examples of the polymers are polyvinyl pyrrolidone, polyvinyl acetate, polyvinyl propionate, polyvinyl butyral, polyvinyl chloride, polyacrylic acid ester, polymethacrylic acid ester, nitrocarboxymethyl cellulose, N-vinyl pyrrolidone-acrylic acid copolymer, N-vinyl pyrrolidone-acrylic acid-methyl acrylate copolymer, vinyl phthalimide-acrylic acid copolymer, cellulose acetate hydrogen phthalate, poly-N-methyl methacrylamide, dimethylaminoethyl methacrylate-acrylic acid copolymer, etc.

In general, for dispersing to form fine droplets of the dye releasing type redox compound, a colloid mill, a high-pressure homogenizer, an ultrasonic emulsifying means, etc., may be used or an anionic surface active agent can be used as an emulsifying aid, for example, sodium dodecylbenzenesulfonate.

Examples of the hydrophilic colloid used for dispersing the dye releasing redox compound of this invention are, for instance, gelatin; colloidal alubmin; casein; cellulose derivatives such as carboxymethyl cellulose, hydroxyethyl cellulose, etc.; saccharose derivatives such as agar-agar, sodium alginate, starch derivatives, such as dextrin etc.; synthetic hydrophilic colloids such as polyvinyl alcohol, poly-N-vinyl pyrrolidone, polyacrylic acid copolymers, such as copolymers of acrylic acid and an acrylate or copolymers of acrylic acid and vinyl pyridine, polyacrylamide, and partially hydrolyzed products thereof. If desired, a compatible mixture of these polymers can be used. Among these hydrophilic colloids, gelatin is most generally used but gelatin may be partially or wholly replaced by a synthetic polymer or synthetic polymers.

A photosensitive element for color diffusion transfer process has a silver halide emulsion layer and associated therewith the dye releasing redox compound.

The silver halide emulsion used in this invention is a hydrophilic colloid dispersion of silver chloride, silver bromide, silver chlorobromide, silver iodobromide, silver chloroiodobromide, or a mixture thereof. The halogen composition of the silver emulsion is selected according to the purpose of the color photographic materials and the processing conditions, but a silver chloroiodobromide emulsion containing 1 to 10 mole% iodide (less than 30 mole% chloride), the balance being bromide, is particularly preferred. The grain size of the silver halide used may be an ordinary grain size or a fine grain size, but generally a silver halide having a mean grain size of from about 0.1 micron to about 2 microns is preferred. Furthermore, according to the purpose of the color photographic material, the use of a silver halide having uniform grain size is preferred. The form of the silver halide grains used may be cubic octahedal, or a mixed crystal system.

The silver halide emulsions used in this invention may be prepared in a conventional manner as described in, for instance, P. Glafkides; "Chimie Photographique", 2nd Edition, Paragraphs 18-23, published by Paul Montel, Paris in 1957. It is preferred that the silver halide emulsion used in this invention be chemically sensitized by a natural sensitizer contained in gelatin, a sulfur sensitizer such as sodium thiosulfate or N,N,N'-triethylthiourea, a gold sensitizer such as a thiocyanate complex salt of monovalent gold and a thiosulfate complex salt of monovalent gold, or a reducing sensitizer such as stannous chloride or hexamethylene tetramine. In this invention, a silver halide emulsion which forms a latent image on the surface of the grains or an internal latent image silver halide emulsion as described in U.S. Pat. Nos. 2,592,550 and 3,206,313 as well as a direct reversal silver halide emulsion using a sensitizer can be used.

The silver halide emulsion used in this invention may be stabilized by conventional additives such as 4-hydroxy-6-methyl-1,3,3a,7-tetraazaindene, 5-nitroimidazole, 1-phenyl-5-mercaptoetrazole, 8-chloromercury quinone, benzenesulfinic acid, pyrocatechin, 4-methyl-3-sulfoethylthiazolidine-2-thion. Furthermore, inorganic compounds such as the complex salt of a platinum group metal, e.g., a chlorocomplex salt of palladium, etc.; a cadmium salt, and a mercury salt are also useful for stabilization of the silver halide emulsion used in this invention. Moreover, the silver halide emulsion used in this invention may contain a sensitizing compound such as a polyethylene oxide compound.

The silver halide emulsion used in this invention may have, if desired or necessary, its color sensitivity enlarged by the action of a spectral sensitizing dye; examples of useful spectral sensitizing dyes used for this purpose are cyanine dyes, merocyanine dyes, homopolacyamine dyes, styryl dyes, hemicyanine dyes, oxonol dyes, and hemioxonole dyes.

Specific examples of useful spectral sensitizing dyes are described in P. Glafkides; "Chimie Photographique"; 2nd Edition, Chapter 5 35–41 and in F. M Hamer; "The Cyanine Dyes and Related Compounds", Interscience. Cyanine dyes where the nitrogen atom of the basic heterocyclic nucleus thereof has been substituted by an aliphatic group (e. g., an alkyl group) having a hydroxyl group, a carboxyl group, or a sulfo group as described in, for instance, U.S. Pat. Nos. 2,503,776; 3,459,553; and 3,177,210 are particularly useful for the practice of this invention.

The photosensitive element of the color diffusion transfer photographic material of this invention is prepared by coating the silver halide emulsion on a plancar support which does not undergo severe dimensional deformation during processing, such as a cellulose acetate film, a polystyrene film, a polyethylene terephthalate film, a polycarbonate film, a laminate of these films, and a thin glass sheet as is generally used for photographic materials.

If the support has insufficient adhesive power to the silver halide emulsion, a subbing layer having a good adhesive power to both elements is formed on the support. Futhermore, to improve the adhesive property of the support, the surface thereof may be subject to a pre-treatment such as a corona discharge treatment, an ultraviolet irradiation treatment, and a flame treatment.

Moreover, a paper, a baryta-coated paper, or a paper coated with a water-impermeable polymer such as polyethylene can be used as the support.

The dye releasing redox compounds of this invention may be used in general color photographic materials but can also be advantageously used in diffusion transfer color photographic materials. In the latter case, color photographic units having the unit constructions as described in Japanese Patent Publication 16.356/1971, Japanese Patent Application No. 10,640/1974, and U.S. Pat. No. 3,594,164 can be used.

In the color photographic element of this invention, a silver halide emulsion is associated with the aforesaid dye releasing redox compound. A combination of a specific color sensitivity of the silver halide emulsion and a specific spectral absorption of the dye image is selectively employed according to the desired color reproduction. For natural color reproduction by subtractive color photography, at least two combinations each of a silver halide emulsion having a selective spectral sensitivity in a certain wave length region and a compound providing a dye image having a selective spectral absorption in the same wave length region are employed. A particularly useful photosensitive element comprises a combination of a blue sensitive silver halide emulsion and a yellow dye releasing redox compound, a combination of a green sensitive silver halide emulsion and a magenta dye releasing redox compound, and a combination of red sensitive silver halide emulsion and a cyan dye releasing redox compound. Thse combination units of silver halide emulsions and dye releasing redox compounds may be in a multilayer structure in a face-to-face relationship or may be in one layer as a mixture of fine particles of each of the units. In a preferred multi-layer structure of a color photographic element, a blue sensitive emulsion layer, a green sensitive emulsion layer, and a red sensitive emulsion layer are disposed in this order from the exposure side, and when highly sensitive silver halide emulsions containing silver iodide are used, it is preferred to dispose a yellow filter layer between the blue sensitive silver halide emulsion layer and the green sensitive silver halide emulsion layer.

The yellow filter layer used for this purpose can contain a dispersion of yellow colloidal silver, for example, a Carey Lea colloidal silver yellow filter, a dispersion of an oil soluble yellow dye, an acid dye mordanted to a basic polymer or a basic dye mordanted to an acid polymer.

It is advantageous that the silver halide emulsion layers be isolated by interlayers from each other. The interlayer contributes to prevent an undesirable coaction between differently color sensitized silver halide emulsion layers. The interlayer is usually composed of a hydrophilic polymer such as gelatin, polyacrylamide, partially hydrolyzed polyvinyl acetate or a porous polymer formed from a latex of a hydrophilic polymer and a hydrophobic polymer as described in U.S. Pat. No. 3,625,685, or further a polymer which gradually increases in hydrophilicity by the action of a processing composition, such as calcium alginate as described in U.S. Pat. No. 3,384,483.

The dye releasing redox compound of this invention is used in an amount of about 50 to about 0.5, preferably 10 to 2, molar times the amount of the dye releasing redox compound based on silver in the silver halide emulsion associated therewith.

When the present invention is applied to a diffusion transfer system, the aforesaid photosensitive element containing the dye releasing redox compound or compounds is superimposed on an image receiving layer in a face-to-face relationship and, after image-wise exposure, the photographic assembly is processed by spreading an alkaline processing solution between both elements. In this case, the image receiving element may be separated from the photosensitive element after the image transfer is finished, or, as is described in U.S. Pat. No. 3,415,645, or a transparent support can be employed as the support for the image receiving element, and a reflecting layer disposed between the image receiving layer and the photosensitive layer, the dye image thus transferred to the image receiving layer being observed without stripping the photosensitive element.

In the color diffusion transfer system, it is necessary that the image receiving layer have a mordant layer. The exact mordant layer material selected is not overly important, and there can be used any compound which has a mordanting or fixing effect for dyes. However, since, in general, the dyes used in the present invention are acidic dyes, basic polymers are more effectively used as mordants. For instance, preferred mordants are disclosed in U.S. Pat. Nos. 1,366,869 and 2,882,156, in Belgian Pat. No. 729,202 and in U.S. Pat. Nos. 2,484,480, 3,271,148 and 3,271,147. The mordant layer may be composed of, for instance, a latex of poly-4-vinylpyridine (in particular, in polyvinyl alcohol), polyvinyl pyrrolidone, or a polymer containing a quaternary ammonium salt as described in U.S. Pat. No. 3,239,337, and, in this case, it is preferred that the image receiving element have the function of neutralizing alkali carried from the liquid processing composition at development. While not mandatory, generally excellent results are obtained when the polymer used in the mordanting layer has a molecular weight of from about 10,000 to about 100,000. The processing composition contains an alkali to provide a sufficiently high pH, ordinarily higher than 10, preferably higher than 11, for promoting the image forming process comprising the development of silver halide emulsions and the diffusion of the dyes released from the dye releasing redox compounds. After the formation of the dye images by diffusion transfer is substantially finished, the pH of the film unit is controlled to about neutral, that is, to below about 9, preferably below about 8, to substantially stop the further progress of the image forming step, whereby the occurence of changes of the dye image with the passage of time is prevented and the occurence of discoloring and fading of images and the formation of stains in blank areas due to high alkalinity are prevented. For this purpose, it is preferred to employ a neutralizing layer containing an acid material in a sufficient amount to neutralize the pH of the alkaline processing composition used for the development treatment, that is, an acid material in a real concentration of greater than the equivalent of the alkali in the liquid processing composition spread in the film unit. It should be noted, in this regard, that the pH is not always 7, rather, the pH varies depending upon the nature of any spacer layer used; in general, however, it is about 5 to 8. The preferred acid material is a material containing an acid group having a pKa of less than 9 or a precursor providing such an acid group by hydrolysis. Examples of such preferred acid materials are the higher fatty acids such as oleic acid as described in U.S. Pat. No. 2,983,606 and the polymers of acrylic acid, methacrylic acid or maleic acid and the partial esters or acid anhydrides thereof as described in U.S. Pat. No. 3,362,819. Specific examples of the polymeric acid materials used for the neutralizing layer are a copolymer of maleic anhydride and a vinyl monomer such as ethylene, vinyl acetate, vinyl methyl ether, etc.; the n-butyl half esters of such copolymers; a copolymer of butyl acrylate and acrylic acid; cellulose acetate acid phthalate; etc. It is most preferred that the amount of hydrogen which is effectively released to function as an acid is preferably from about 3 to about 15 g per 1 Kg of such polymers. The neutralizing layer may further contain a polymer such as cellulose nitrate and polyvinyl acetate and also a plasticizer as described in U.S. Pat. No. 3,557,237 in addition to the aforesaid acid material. Furthermore, the neutralizing layer may be hardened by cross-linking with a polyfunctional aziridine compound or an epoxy compound. The neutralizing layer may be disposed in the image receiving element and/or the photosensitive element of the film unit; it is particularly preferred that the layer be disposed between the support for the image receiving element and the image receiving layer thereof. Still further, the acid material may be incorporated in the film unit as microcapsules thereof as described in German Patent Application (OLS) 2,038,254.

In this case, it is preferred that the neutralizing layer (or acid material containing layer) be isolated from the spread layer of the processing composition by a neutralization rate controlling layer. The neutralization rate controlling layer functions as follows; that is, by the action of the aforesaid neutralizing layer an undesirable reduction in the density of the transferred image by a too rapid reduction in the pH of the processing composition before the completion of the development of silver halide emulsion layers and the formation of the transferred image is prevented and the pH of the processing composition is reduced after the desired development of silver halide emulsion layers and transfer of dye images are finished.

In a preferred embodiment of this invention, the image receiving element of the film unit has a multilayer structure comprising a support, a neutralizing layer, a neutralization rate controlling layer, and a dyeable layer (or image receiving layer). The neutralization rate controlling layer is mainly composed of a polymer such as gelatin, polyvinyl alcohol, polyvinyl propyl ether, polyacrylamide, hydroxypropylmethyl, cellulose, isopropyl cellulose, partially hydrolyzed polyvinyl butyral, partially hydrolyzed polyvinyl acetate, where for hydrolyzed materials such as polyvinyl acetate the degree of hydrolysis is preferbly above about 80%, more preferably from 88 to 100% or a copolymer of β-hydroxyethyl methacrylate and ethyl acrylate. The polymer layer may be hardened by cross-linking using an aldehyde compound such as formaldehyde or a N-methylol compound. The neutralization rate controlling layer preferably has a thickness of from about 2 microns to about 20 microns.

The thickness of the various layers, be they be mandatory or optional, used in the present invention are not overly limited. However, in general, the thickness of any layer used in the present invention is about 0.5 to about 30μ, with preferred thicknesses for a light-sensitive layer, a mordanting layer, a spacer layer and an acidic polymer layer being 0.5 to 3μ, 3 to 20μ, 3 to 20 and 5 to 20μ, respectively.

For commercial systems, generally speaking a processing solution will always contain an alkali such as sodium hydroxide, potassium hydroxide, etc., and a viscosity increasing agent such as hydroxyethylcellulose, carboxymethylcellulose, etc.

The processing composition used for the development of the color photographic materials of this invention is an aqueous liquid composition containing processing components necessary for developing silver halide emulsions and the formation of transferred dye images or remaining dye images after releasing dyes. The medium used for the processing composition is mainly water but it can contain, as the case may be, a hydrophilic solvent such as methanol, 2-methoxy ethanol, etc. Conventionally, such hydrophilic solvents are used in an amount less than 50% by weight of the total solvent. The processing composition contains an alkali in an amount sufficient to maintain the pH necessary for causing the development of the silver halide emulsion layers and an neutralizing the acid (e.g., a hydrohalogenic acid such as hydrobromic acid, etc.,) formed during the development and the dye image forming processes. Examples of the alkali are alkali metal salts, alkaline earth metal salts, and amines such as lithium hydroxide, sodium hydroxide, potassium hydroxide, a calcium hydroxide dispersion, tetramethylammonium hydroxide, sodium carbonate, sodium tertiary phosphate, diethylamine, etc. When the processing composition is used in a diffusion transfer process, it is desirable that the processing composition contain an alkali hydroxide to provide a pH of higher than about 12, preferably higher than 13, at room temperature. formation transferred For a diffusion transfer process, the processing composition preferably contains a hydrophilic polymer such as a high molecular weight polyvinyl alcohol, hydroxyethyl cellulose, sodium carboxymethyl cellulose, etc. The polymer serves to provide a viscosity of higher than 1 poise, preferably of 500 to 1,000 poise at room temperature, to the processing composition to enable uniform spreading of the processing composition at development and to form a non-fluid film layer when the processing composition is concentrated by the transfer of the aqueous medium to the photosensitive element and the image receiving element to serve to unify the film unit after processing. The polymer film thus formed can also contribute to control the further transfer of colored components into the image receiving layer to prevent the occurence of discoloring of dye image formed after the formatin of the transfered dye images is substantially completed.

The processing composition may further contain, as desired or necessary, a light absorbing material such as carbon black to prevent the silver halide emulsion layers of the photosensitive element from being fogged by external light during processing and also the desensitizers as described in U.S. Pat. No. 3,579,333 for the same purpose in addition to the aforesaid components.

The dye releasing redox compound of this invention represented by the aforesaid general formula can be prepared by the reaction of a sulfonyl chloride of an azo dye and an o-aminophenol derivative having an organic ballast group. Also, the dye moieties and the sulfonyl chlorides thereof them can be prepared in the manner as described in Japanese Patent Applications (OPI) Nos. 12,581/1973, 33,826/1973, 114,424/1974, and 126,332/1974.

Specific examples of preparing some of the dye releasing redox compounds used in this invention are illustrated below. Unless otherwise indicated, in the following Synthesis Examples, all percentages are weight percentages and all processings are conducted at room temperature.

SYNTHESIS EXAMPLE 1 a. Synthesis of dimethanesulfonyl toluhydroquinone

In 500 ml. of pyridine was dissolved 124 g. of toluhydroquinone and then 170 ml. of methanesulfonyl chloride was added dropwise to the solution while stirring at a temperature below 25° C. Thereafter, the mixture was further stirred for one hour at room temperature. After the reaction was over, 500 ml. of chloroform was added to the reaction mixture and the resultant mixture was washed several times with water, then with 10% hydrochloric acid and finally once with water. The chloroform layer formed was recovered and dried over anhydrous sodium sulfate. After filtering, the solvent was distilled off from the filtrate and the residue formed was recrystallized from methanol to provide 230 g. of the desired compound of a melting point of 80° to 82° C.

b. Nitration of dimethanesulfonyl toluhydroquinone

In 350 ml. of concentrated sulfuric acid (98 wt. %) was dispersed 140 g. of dimethanesulfonyl toluhydroquinone and then a mixture of 40 ml. of 60% nitric acid and 40 ml. of concentrated sulfuric acid (98 wt. %) was added dropwise to the dispersion while stirring at a temperature of 5°–10° C. Thereafter, the mixture was further stirred for one hour. After the reaction was over, the reaction mixture was poured into ice water and the crystals formed were recovered by filtration. The crystals were well washed with water and recrystallied from a mixture of methanol and acetonitrile to provide about 130 g. of the desired nitrated product.

c. Synthesis of 2-nitro-4-methanesulfonyloxy-5-methylphenol:

In one liter of hot acetonitrile was dissolved 97.5 g. of the nitrated product obtained in the above process, and, after cooling the solution to about 30° to 40° C., a solution of 20 g. of sodium hydroxide in 100 ml. of water was added to the solution while stirring. The mixture was further stirred for about 30 minutes at 30° to 40° C. After the reaction was over, the reaction mixture was poured into ice water and the mixture was acidified to below pH 1 with hydrochloric acid to form crystals, which were recovered by filtration, washed with water and then methanol, and dried to provide 66 g. of the desired product having a melting point of 134°–136° C.

d. Benzylation of 2-nitro-4-methanesulfonyloxy-5-methyl-phenol:

In 800 ml. of acetone was dissolved 66 g. of 2-nitro-4-methanesulfonyl-oxy-5-methylphenol thus prepared and then, after adding to the solution 108 g. of potassium carbonate and 53 g. of benzyl bromide while stirring, the mixture was refluxed for 3 hours. After the reaction was over, the reaction mixture was filtered under suction at elevated temperature (50°–60°) and then the filtrate thus obtained concentrated. The concentrate was allowed to cool and the crystals formed recovered by filtration and washed with ether to provide 55 g. of the benzylated product having a melting point of 117° to 118° C.

e. Synthesis of 2-methyl-4-benzyloxy-5-nitrophenol:

In 200 ml. of methanol was dissolved 36 g. of the product obtained in the above process d) and, after adding to the solution a solution of 10 g. of sodium hydroxide in 10 ml. of water, the mixture was refluxed for one hour. After the reaction was over the reaction mixture was allowed to cool, and, after acidifying the reaction mixture to below pH 1 with concentrated hydrochloric acid, water was gradually added to the system until the formation of crystals stopped, whereafter the addition of water was stopped and the crystals were recovered by filtration to provide 28 g. of the desired product having a melting point of 65° to 68° C.

f. Hexadecylation of 2-methyl-4-benzyloxy-5-nitrophenol:

A mixture of 26 g. of 2-methyl-4-benzyloxy-5-nitrophenol obtained in the above process e), 120 ml. of acetone, 30 g. of potassium carbonate, and 31 g. of cetyl bromide was refluxed for 8 hours with stirring. After the reaction was over, the reaction mixture was filtered under suction and then methanol was added to the filtrate to form crystals, which were recovered by filtration to provide 39 g. of the desired product having a melting point of 52° to 53° C.

g. Synthesis of 2-amino-4-hexadecyloxy-5-methyl-phenol:

To 24 g. of the product obtained in process (f) were added 500 ml. of ethanol and 10% palladium carbon (Pd-C catalyst) in an autoclave and then the product was hydrogenated for 6 hours at 50° C. and 50 atms. After cooling, the reaction product was recovered from the autoclave and, after removing the catalyst, about ⅔ of the ethanol was distilled off from the product to obtain 16 g. of the crystals of the desired product having a melting point of 92° to 95° C.

h. Synthesis of 1-(p-chlorosulfonylphenyl)-3-(N-n-hexylcarboxamido)-4-(p-sulfamolyphenylazo)-5-pyrazolone:

To 50 ml. of ice-cooled chlorosulfonic acid was gradually added 20 g. of 1-phenyl-3-(N-n-hexylcarboxamido)-4-(p-sulfamoylphenylaxo)-5-pyrazolone with stirring, and then the mixture was further stirred for one hour at room temperature. The reaction mixture was poured onto 1 kg. of chipped ice and the crystals formed were recovered by filtration, airdried, and recrystallied from actone to provide 21 g. of the desired product having a melting point of 233° to 240° C.

i. Synthesis of Compound 1:

Into 100 ml. of tetrahydrofuran was dispersed 3 g. of 1-(chlorosulfonylphenyl)-3-(N-n-hexylcarboxamido)-4-(p-sulfamoylphenylazo)-5-pyrazolone produced in the above process (h), and, after adding thereto 2.5 g. of the amine obtained in process (g) and 4 ml. of pyridine, the mixture was stired for 3 hours at room temperature. After the reaction was over, ther reaction mixture was poured into water and the crystals thus formed were recovered by filtration and washed with cold methanol to provide 4 g. of Compound 1 having a melting point of 205°–210° C.

SYNTHESIS EXAMPLE 2 a. Synthesis of 2-amino-4-sulfonyloxy-5-methylphenol:

Into 1,200 ml. of hot ethanol (70°–80° C) was dissolved 200 g. of 2-nitro-4-sulfonyloxy-5-methylphenol obtained in process (c) of Synthesis Example 1 and then a solution of 450 g. of sodium hydrosulfite in water was gradually added to the solution. When the yellow color of the mixture vanished, which showed the finish of the reaction, the reaction mixture was poured into ice water and the colorless crystals formed were recovered by filtration and dried to provide 125 g. of the desired product having a melting point of 129° to 130° C.

b. Acetylation of 2-amino-4-sulfonyloxy-5-methylphenol:

After ice cooling 300 ml. of acetic anhydride in a three necked flask, 95 g. of 2-amino-4-sulfonyloxy-5-methylphenol was gradually added with stirring. The mixture was stirred for about 30 minutes while ice cooling and then for 30 minutes at room temperature to form crystals, which were recovered by filtration and washed well with ether to provide about 90 g. of 2-acetamino-4-sulfonyloxy-5-methylphenol having a melting point of 193° to 196° C.

c. Synthesis of 2-acetamino-4-sulfonyloxy-5-methyl-6-chlorophenol:

Into 300 ml. of acetic acid was dispersed 90 g. of the 2-acetamino-4-sulfonyloxy-5-methylphenol obtained in the above process b), and then 35 ml. of sulfuryl chloride was added dropwise to the dispersion while stirring at room temperature. It is preferred to perform the addition of the chloride at temperatures below 30° C. Thereafter, the mixture was stirred for about 30 minutes and the reaction mixture filtered and washed with water to provide 95 g. of the desired compound having a melting point of 135° to 137° C.

d. Benzylation of 2-acetamino-4-sulfonyloxy-5-methyl-6-chlorophenol:

Into acetone was dissolved 95 g. of the product obtained in the above process (c), and, after adding thereto 200 g. of potassium carbonate and 120 g. of benzyl bromide, the mixture was refluxed for 2 hours with stirring. The reaction mixture was then filtered under suction at elevated temperature (50°- 60° C) and the filtrate was concentrated to form crystals, which were recovered by filtration to provide about 85 g. of the desired benxylation product having a melting point of 125° to 128° C.

e. Synthesis of 2-methyl-3-chloro-4-benzyloxy-5-acetaminophenol:

Into 400 ml. of hot ethanol (70°- 80° C.) was dissolved 60 g. of the compound obtained in the above process (d), and, after adding thereto a solution of 20 g. of sodium hydroxide in 100 ml. of water, the resultant mixture was refluxed for 30 minutes. After cooling, the reaction mixture was poured into ice water and then acidified to below pH 1 by hydrochloric acid to form crystals, which were recovered by filtration and recrysallized from methanol to provide 45 g. of the desired product having a melting point of 180°- 182° C.

f. Hexadecylation of 2-methyl-3-chloro-4-benzyloxy-5-acetaminophenol:

Into 350 ml. of acetone was dissolved 41 g. of the compound obtained in process (e) above, and, after adding thereto 50 g. of cetyl bromide and 90 g. of potassium carbonate, the mixture was refluxed for 6 hours. After the reaction was over, the reaction mixture was filtered under suction at elevated temperature (50°- 60° C.) and the filtrate concentrated. By adding methanol to the concentrate, crystals formed, which were recovered by filtration to provide 45 g. of the desired hexadecyl ether having a melting point of 77° to 79° C.

g. Synthesis of 2-amino-4-hexadecyloxy-5-methyl-6-chlorophenol:

Into 150 ml. of acetic acid was dispersed 20 g. of the compound obtained in the above process (f), and, after adding thereto 50 ml. of concentrated hydrochloric acid, the mixture was refluxed for 30 minutes. The reaction mixture obtained was allowed to cool and further cooled with ice to form precipitates, which were recovered by filtration to provide about 12 g. of 2-amino-4-hexadecyloxy-5-methyl-6-chlorophenol. Then, by recrystallizing the crude product from acetonitrile, 10 g. of the pure product having a melting point of 136° to 140° C. was obtained.

h. Synthesis of 2-(p-chlorophenylazo)-5-chlorosulfonyl-8-acetamino-1-naphthol:

Into a mixture of 106 ml. of water and 53 ml. of p-chloroaniline was dessoved 26.5 g. of p-chloroaniline and then a solution of 13.8 g. of sodium nitrite in 40 ml. of water was dropwise added to the solution while stirring and controlling the addition rate of the solution so that the temperature of the reaction system was not over 5° C. In 400 ml. of water was dissolved 49.2 g. of sodium acetate and then 400 ml. of dimethylformamide (DMF) was added to the solution. Then, 60.6 g. of sodium acetyl S-acid was dissolved in the mixture. Thereafter, the diazonium solution prepared in the aforesaid process was dropwise added to the mixture while stirring and then the resultant mixture was stirred for 30 minutes at room temperature. The reaction was further continued for 2 hours at room temperature. Then, 1 liter of an aqueous 30% sodium chloride solution was added to the reaction mixture and the mixture heated to about 60° C. to form crystals, which were recovered by filtration to provide 67 g. of 2-(p-chlorophenyazo)-5-sodium-sulfo-8-acetamino-1-naphthol having a melting point of higher than 300° C.

Then, in a 500 ml. three necked flask equipped with a stirrer, a thermometer, and a calcium chloride-containing tube (drying tube) were placed 150 ml. of chlorosulfonic acid and 150 ml. of thionyl chloride and the system cooled to 5° C. To the mixture was gradually added 67 g. of 2-(p-chlorophenylazo)-5-sodium-sulfo-8-acetamino-1-naphthol prepared in the above step and the mixture was stirred for one hour at about 60° C. The reaction mixture obtained was cooled to 10° C. and was added dropwise to about 2 kg. of ice water with stirring to form crystals, which were recovered by filtration and washed with water. The crystals thus obtained were washed in 2 liters of acetonitrile, recovered by filtration, and dried to provide 53 g. of the desired compound having a melting point of 200° to 204° C.

The sodium acetyl S-acid used in the process is the compound shown by the formula

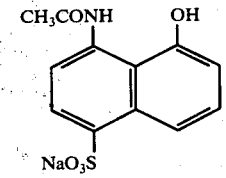

i. Synthesis of Compound 3:

Into 100 ml. of tetrahydrofuran was dispersed 4.4 g. of 2-(p-chlorophenylazo)-5-chlorosulfonyl-8-acetamino-1-naphthol prepared in the above process (h), and, after adding thereto 4.1 g. of the compound obtained in the above process (g) and 50 ml. of pyridine, the mixture was stirred for 3 hours at room temperature. After the reaction was over, the reaction mixture was poured into ice water and the crystals formed were recovered by filtration and recrystallized from a mixture of tetrahydrofuran and acetonitrile to provide about 2 g. of Compound 3 having a melting point of 134° to 138° C.

SYNTHESIS EXAMPLE 3 a. Synthesis of 2-(1',1'-dimethyl-3',3'-dimethylbutyl)-4-n-hexyloxyphenol:

To 30 ml. of methanol were added 58 g. of 4-(n-hexyloxy)phenol and 35 g. of diisobutylene and the mixture was stirred for 30 minutes at about 50° C. Then, 24 ml. of 93% sulfuric acid was dropwise added to the mixture over a period of about one hour (60° to 70° C), and, then, after raising the temperature of the reaction mixture to 90° C., the mixture was further stirred for 4 hours. After cooling, 200 ml. of benzene was added to the reaction mixture and the resultant mixture was washed with water. Then, after distilling off benzene under reduced pressure, the residue was distilled at 155° to 160° C. and 0.5 mm. Hg to provide 40g. of the desired product.

b. Synthesis of 2-nitro-4-n-hexyloxy-6(1',1'-dimethyl-3',3'-dimethylbutyl)phenol:

To 100 ml. of glacial acetic acid was added 30 g. of the product obtained in process (a) above and the mixture was stirred for 15 min. at 15° to 20° C. Then, a mixture of 7.6 ml. of 60% nitric acid and 50 ml. of glacial acetic acid was dropwise added to the mixture. Thereafter, the mixture was stirred for one hour and the reaction mixture obtained was poured onto about 1 liter of ice water. The crystals thus formed were recovered by filtration, washed with water, dried and recrystallized from benzene to provide 28 g. of the desired product.

c. Reduction of nitro group:

To 300 ml. of ethanol was added 28 g. of the product obtained in the above process (b), and the mixture was maintained at 60° to 70° C for 15 minutes, whereafter to the mixture was added a mixture of 80 g. of sodium hydrosulfite and 500 ml. of water and the resultant mixture was stirred for 5 minutes at 80° to 90° C. Then, about 150 ml. of benzene was distilled off from the reaction mixture under reduced pressure and the residue was cooled, whereby the desired amino product formed. The product was recovered by filtration and dried to give 20 g. of the amino product.

d. Synthesis of Compound 5:

To 300 ml. of tetrahydrofuran was added 16 g. of the amino product obtained in the above process (c) and 27 g. of 1-(p-chlorosulfonylphenyl)-3-(N-butycarboxamido)-4-(p-sulfamoylphenylazo)-5-pyrazolone and the mixture was stirred at room temperature for 5 minutes. To the mixture was added 30 ml. of pyridine and the resultant mixture was stirred for 8 hours at room temperature. The reaction mixture was added to 2 liters of 0.5 N hydrochloric acid and the tarry material formed was recovered and recrystallized from a mixture of ethyl acetate and methanol to provide 35 g. of Compound 5.

SYNTHESIS EXAMPLE 4 (COMPOUND 9)

Into 100 ml. to tetrahydrofuran were dispersed 7.2 g. of 2% amino-4-hexadecyloxy-5-methylphenol and 5.5 g. of 1-(p-chlorosulfonylphenyl)-3-(N-hexylcarboxamido)-4-(p-chlorosulfonylphenylazo)-5-pyrazolone obtained in producing Compound 1 in Synthesis example 1, and, after adding thereto 12 ml. of pyridine, the mixture was stirred for 3 hours at room temperature. After the reaction was over, the reaction mixture was added to 200 ml. of methanol and 100 ml. of cold 5% hydrochloric acid (at 10° to 20° C) was gradually added to the reaction mixture while, if necessary, adding thereto pieces of ice to form crystals, which were recovered by filtration and recrystallized from a mixture of ethyl acetate and methanol to provide about 6.8 g. of the pure desired compound having a melting point of 210° to 216° C.

SYNTHESIS EXAMPLE 5 (COMPOUND 10)

Into 100 ml. of pyridine were dispersed 7.2 g. of 2-amino-4-hexadecyloxy-5-methylphenol and 5.2 g. of 2-(p-chlorosulfonyl-phenylazo)-5-chlorosulfonyl-8-acetamino-1-naphthol obtained in producing Compound 1 in Synthesis example 1 and the dispersion was stirred for 6 hours at room temperature, whereby the compounds in the dispersed state gradually dissolved. After the reaction was over, the reaction mixture was poured into ice water and the crystals formed were recovered by filtration and recrystallized from a mixture of tetrahydrofuran and acetonitrile to provide 5.5 g. of the desired product having a melting point of 199° to 203° C.

SYNTHESIS EXAMPLE 6 (Compound 12)

a. Dimethanesulfonylation of pentadecyl hydroquinone:

Into 1 liter of pyridine was dissolved 322 g. of pentadecyl hydroquinone and then 180 ml. of methansulfonyl chloride was dropwise added to the solution while stirring at 25° to 30° C. Thereafter, the mixture was further stirred for 2 hours at the same temperature. After the reaction was over, the reaction mixture was poured into ice water to form crystals, which were recovered by filtration and recrystallized from ethyl acetate to provide 406 g. of dimethanesulfonyloxypentadecyl hydroquinone.

b. Nitration of dimethanesulfonyloxypentadecyl hydroquinone:

Into 1 liter of galcial acetic acid was dissolved 240 g. of the compound obtained in the above process (a), and, after dropwise adding to the solution 40 ml. of 61% nitric acid with stirring at about 10° C., the mixture was stirred for one hour. The reaction mixture thus obtained was poured into ice water to form crystals, which were recovered by filtration and washed with water to provide 223 g. of the nitro product.

c. Synthesis of 2-nitro-4-methanesulfonyloxy-5-pentadecylphenol:

Into 1.5 l. of acetonitrile was dispersed 260 g. of the compound obtained in the above process (b), and, after adding to the dispersion an aqueous solution of 30 g. of sodium hydroxide in 100 ml. of water, the mixture was stirred for one hour at 50° to 60° C. The reaction mixture obtained was added to ice water and acidified to below pH 1 with hydrochloric acid to form crystals, which were recovered by filtration and recrystallized from acetonitrile to provide 155 g. of the desired product having a melting point of 96° to 102° C.

d. Benzylation of 2-nitro-4-methanesulfonyloxy-5-pentadecylphenol:

A mixture of 120 g. of the compound obtained in the above process (c), 108 g. of potassium carbonate, 53 g. of benzyl bromide, and 800 ml. of acetone was refluxed while heating for 10 hours with stirring. Then, the reaction mixture was filtered under suction while it was hot (50° to 60° C) and the filtrate concentrated to about ⅔'s of its original volume and then allowed to cool to form crystals, which were recovered by filtration and washed with methanol to provide about 60 g. of the desired compound having a melting point of 88° to 93° C.

e. Synthesis of 2-pentadecyl-4-benzyloxy-5-nitrophenol:

Into 2 liters of ethanol was dispersed 133 g. of the compound obtained in the above process (d), and, after adding to the dispersion a solution of 15 g. of sodium hydroxide in 100 ml. of water with stirring, the mixture was refluxed for 3 hours. The reaction mixture thus obtained was added to ice water and acidified to below pH 1 by hydrochloric acid to form crystals, which were recovered by filtration to provide 86 g. of the desired compound.

f. Ethylation of 2-pentadecyl-4-benzyloxy-5-nitrophenol:

A mixture of 116 g. of 2-pentadecyl-4-benzyloxy-5-nitrophenol 90 g. of potassium carbonate, 60 g. of ethyl iodide, and 700 ml. of acetone was refluxed for 8 hours while stirring. After the reaction was over, the reaction mixture was filtered while hot (50° to 60° C) and the filtrate concentrated to form precipitates of the desired product, which were recovered by filtration and washed with methanol to give 55 g. of the desired product.

g. Synthesis of 2-amino-4-ethoxy-5-pentadecylphenol:

To 55 g. of the compound obtained in process (f) above were added 400 ml. of ethanol and 2 g. of 10% palladium carbon (Pd-Catalyst) in a one liter autoclave and the compound was hydrogenated for 3 hours at 50° C. at 50 atm. After allowing the reaction mixture to cool overnight the product was recovered from the autoclave. The catalyst was removed from the reaction mixture by filtration and the filtrate allowed to cool to form crystals, which were recovered by filtration and washed with methanol to provide 28 g. of the desired product.

h. Synthesis of Compound 12:

Into 150 ml. of tetrahydrofuran was dispersed 5.6 g. of 1-(p-chlorosulfonylphenyl)-3-(N-n-hexylcarboxamido)-4-(p-sulfamoyl-phenylazo)-5-pyrazolone obtained in Synthesis example 1, and, after adding to the dispersion 3.5 g. of the amine produced in the above process (g) and 5 ml. of pyridine, the mixture was stirred for 3 hours at room temperature. After the reaction was over, the reaction mixture was added to ice water and the crystals formed were recovered by filtration, washed with methanol, and recrystallized from a mixture of a tetrahydrofuran and acetonitrile to provide 4.2 g. of the desired product having a melting point of 182° to 192° C.

The following examples illustrate the present invention more practically.

EXAMPLE 1

(Test of photographic properties)

A photosensitive element, an image receiving element, and a liquid processing composition were prepared in the following manner.

Photosensitive element:

To a mixture of 20 ml. of N,N-diethyl laurylamide and 60 ml. of cyclohexanone was added 7.5 g. of the yellow dye releasing redox compound (Compound 1) of this invention, and then 3 g. of the compound of the following formula having an average molecular weight of 4000

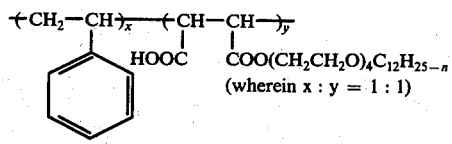

(wherein x : y = 1 : 1)

and 1 g. of sorbitan monolauric acid ester were added to the solution as emusifiers and dissolved therein at about 80° C. The solution was dispersed by emulsification into 210 g. of an aqueous 10 wt. % gelatin solution (containing 0.5% by weight sodium dodecylbenzenesulfonate as an emulsifier) at about 80° C., and then, after adding to the dispersion 200 ml. of water cooled to about 5° C., the mixture was solified by cooling and stored in a refrigerator. Obviously, storage in refrigerator is not mandatory, but such permits the dispersion to be stored for long periods of time with ease. Then, 450 g. of the emulsion was mixed with 250 g. of a red sensitive silver iodobromide emulsion (silver content 0.6 mole/kg; gelatin content 47.5 g./1 kg. emulsion; mean grain size: 1.2 μ) and, after adding thereto 0.4 g. of 2-hydroxy-4,6-dichloro-s-triazine sodium salt as a hardening agent, the mixture was coated on a cellulose triacetate base having a gelatin subbing layer at a coverage of about 170 μg./cm² of silver. A gelatin solution was then coated thereon at a dry thickness of about 1 micron.

Image receiving element:

An image receiving element was prepared by coating a baryta-coated paper with an aqueous solution of 5% by weight gelatin containing 5% by weight of the following polymer as a mordant at a dry thickness of about 6 microns (average molecular weight: about 50,000);

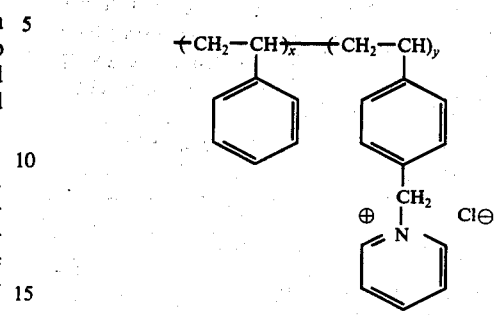

Furthermore, 2-hydroxy-4,6-dichloro-s-triazine sodium salt was incorporated into this polymer layer as a hardening agent in an amount of 1% by weight of the gelatin.

Processing composition:

A processing composition was prepared by stirring the following mixture under an $N_2$ atmosphere.

| Water | 970 | ml. |
|---|---|---|
| Sodium hydroxide | 30 | g. |
| Hydroxyethyl cellulose | 50 | g. |
| Sodium hydrogen sulfite | 0.4 | g. |
| 5-Methylbenzotriazole | 0.4 | g. |
| 1-Phenyl-3-pyrazolidone | 1 | g. |

At processing, the aforesaid photosensitive element was subjected to a white light exposure of 20 CMS through a step wedge (20 stages) of a 0.2 density difference using a 1 Kilowatt tungsten lamp of a color temperature of 2854° K, the photosensitive element was then superposed on the image receiving element, the processing composition prepared above was spread between both elements at a coverage of 1.8 ml./100 cm², and, after 5 minutes, the image receiving element was stripped away, washed with water, and dried. A yellow dye image was thus obtained in the image receiving element by diffusion transfer. When the blue light reflection density of the yellow dye image was measured, the maximum transfer density was 1.43 and the minimum transfer density was 0.38.

EXAMPLE 2

When the same procedure as in Example 1 was followed using Compounds 4, 5 and 7, respectively, in place of the yellow dye releasing redox compound (Compound 1) used in Example 1, a dye image having good photographic properties was obtained in each case.

EXAMPLE 3

The following photosensitive element and the processing composition were prepared and the image forming procedure was performed using an image receiving element having the same construction as in the element used in Example 1.

Photosensitive element;

The photosensitive element was prepared by coating on a cellulose triacetate base having a gelatin subbing layer, in succession, the following layers:

1. Cyan dye releasing layer:

In the same way as in Example 1, 14 g. of the cyan dye releasing redox compound (Compound 17) of this invention was dispersed in the aqueous gelatin solution in place of the yellow dye releasing redox compound (Compound 1) used in Example 1, and then the dispersion was coated on the support at a coverage of about $1.3 \times 10^{-7}$ moles/cm².

2. Red sensitive silver halide emulsion layer:

A red sensitive silver iodobromide emulsion (silver content 0.6 mole/kg.) was coated on the above layer at a coverage of about $1.5 \times 10^{-6}$ moles/cm² of silver.

3. Interlayer:

Following the same procedure as in Example 1, a dispersion was prepared using 30 g. of 2,5-dioctylhydroquinone in place of the yellow dye releasing recox compound (Compound 1) and the dispersion was coated at a coverage of about $3 \times 10^{-7}$ moles/cm² of the compound.

4. Magenta dye releasing layer:

In the same way as in Example 1, 13.5 g. of the magenta dye releasing redox compound (Compound 19) of this invention was dispersed in the aqueous gelatin solution in place of the yellow dye releasing redox compound and the dispersion thus prepared was coated at a coverage of about $1.3 \times 10^{-7}$ moles/cm² of the compound.

5. Green sensitive silver halide emulsion layer;

A green-sensitive silver iodobromide emulsion(silver content 0.6 mole/kg.) was coated at a coverage of about $1.5 \times 10^{-6}$ moles/cm² of silver.

6. Yellow filter layer;

Following the same procedure of preparing the yellow dye releasing redox compound dispersion as in Example 1, a dispersion was prepared using 30 g. of 2,5-dioctylhydroquinone in place of the yellow dye releasing redox compound (Compound 1) and, after mixing 200 g. of the dispersion with 200 g. of an aqeuous solution of 5% by weight gelatin containing 5 g. of Carey Lea type yellow colloidal silver, the mixture was coated at a coverage of about $4 \times 10^{-7}$ moles/cm² of 2,5-dioctylhydroquinone.

7. Yellow dye releasing layer:

Following the same procedure of preparing the cyan dye releasing compound dispersion as in aforesaid layer forming step 1 of this example, a dispersion was prepared using 15 g. of the yellow dye releasing compound (Compound 4) of this invention in place of the cyan dye releasing redox compound and the dispersion was coated at a coverage of about $1.2 \times 10^{-7}$ moles/cm² of the redox compound.

8. Blue sensitive silver halide emulsion layer:

A blue sensitive silver iodobromide emulsion (silver content 0.6 mole/kg.) was coated at a coverage of about $1.5 \times 10^{-6}$ moles/cm² of silver.

9. Protective layer:

An aqueous solution of 5% by weight gelatin was coated at a dry thickness of about 1 micron.

Processing composition:

A processing composition was prepared by mixing the following components under an N₂ atmosphere:

| Water | 970 | ml. |
|---|---|---|
| Sodium hydroxide | 20 | g. |
| Hydroxyethyl cellulose | 50 | g. |
| Sodium hydrogensulfite | 1 | g. |
| 5-Methylbenzotriazole | 0.5 | g. |
| N-Methyl-p-aminophenol . monosulfate | 1.06 | g. |
| N,N-Diethyl-p- | 1.8 | g. |

-continued

| aminophenol . monohydrochloride | | |
|---|---|---|

Using the photosensitive element, the processing composition, and the image receiving element as described above, the same processing as in Example 1 was followed. In this case, however, exposure was to a tungsten lamp (color temperature of 4800° K; 1 Kw; exposure amount: 20 CMS) through a continuous tone wedge where the tramsmission density changed by 0.2 per 1 cm, with a blue filter, green filter or red filter, respectively, and thereafter processed for 15 minutes. Good yellow magenta and cyan transfer dye images were thus obtained, respectively.

EXAMPLE 4

The same procedure as in Example 1 was followed using the photosensitive element and the processing composition shown below and an image receiving element having the same construction as that in Example 1.

Photosensitive element:

The photosensitive element was prepared by coating on a cellulose triacetate base having a gelatin subbing layer, in succession, the following layers:

1. Yellow dye releasing layer:

Same as the yellow dye releasing layer in Example 3.

2. Blue sensitive silver halide emulsion layer:

An internal latent image silver iodobromide emulsion (silver contant 0.59 mole/kg.) containing as a fogging agent the compound of the formula

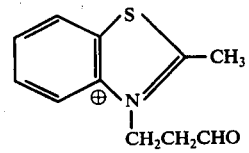

in an amount of 1/100 times by mole ratio per mole of silver was coated at a coverage of about $1.5 \times 10^{-6}$ moles/cm² of silver. The internal latent image silver halide emulsion used was a silver halide emulsion having high internal sensitivity and low surface sensitivity prepared according to the method as described in U.S. Pat. No 2,592,250.

3. Protective layer:

Same as the protective layer in Example 3.

Processing composition:

The processing composition was prepared by stirring the following mixture under a N₂ atmosphere:

| Water | 970 | ml. |
|---|---|---|
| Sodium hydroxide | 20 | g. |
| Hydroxyethyl cellulose | 50 | g. |
| Sodium hydrogen sulfite | 1 | g. |
| 5-Methylbenzotriazole | 0.5 | g. |
| 1-Phenyl-3-pyrazolidone | 1.5 | g. |

Following the same procedure as in Example 1 using the aforesaid photosensitive element, processing composition, and image receiving element, a good yellow positive dye image was formed in the image receiving element by diffusion transfer.

REFERENCE EXAMPLE

The procedure of Example 1 was followed except for using the compound of the following formula (outside the scope of the compounds of this invention) instead of the redox compound of this invention:

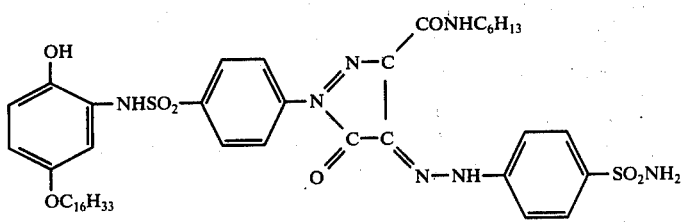

In this case, however, a transferred dye image was not obtained. This shows the effectiveness of the compounds of this invention.

EXAMPLE 5

A photogsensitive element having the same construction as that used in Example 3 was exposed as in Example 3 and developed for 3 minuted using a processing solution having the following composition:

|  |  |
|---|---|
|  | 1,000 ml. |
| Sodium hydroxide | 20 g. |
| Sodium hydrogen sulfite | 1 g. |
| 5-Methylbenzotriazole | 0.5 g. |
| 1-Phenyl-3-pyrazolidone | 2.5 g. |

The element was then blixed for 3 minutes at about 40° C in a blix solution having the following composition and washed with water to provide good cyan, magenta, and yellow dye images.

|  |  |
|---|---|
| Blix solution: |  |
| Water | 1,000 ml. |
| Ferric ethylenediaminetetraacetate | 36 g. |
| Sodium sulfite | 7 g. |
| Ammonium thiosulfate | 100 g. |
| Potassium hydrogen sulfite | 15 g. |
| Sodium phosphate (monobasic) | 20 g. |
| Sodium carbonate monohydrate | 6 g. |

While the invention has been described in detail and with reference to specific embodiments thereof, it will be apparent to one skilled in the art that various changes and modifications can be made therein without departing from the spirit and scope thereof.

What we claim is:

1. A color photographic material comprising a support and at least a silver halide emulsion layer having associated therewith a dye releasing redox compound represented by the general formula

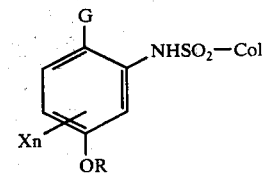

wherein
G represents a hydroxyl group or a group giving a hydroxyl group upon hydrolysis,
Col represents a dye or a group giving a dye, both being diffusible when released upon hydrolysis,
R represents an alkyl group or an aromatic group,
X represents an electron donating group substituent when $n$ is 1 or substituents, which may be the same or different, one of said substituents being an electron donating group and the second or second and third substituents being selected from the group consisting of an electron donating group or a halogen atom when $n$ is 2 or 3, wherein X groups may form a condensed ring, excluding an aromatic hydrocarbon ring, with each other or with OR, $n$ is 1, 2 or 3 and the total carbon number of $X_n$ and R is larger than 8.

2. The color photographic material as set forth in claim 1 wherein said dye releasing redox compound is incorporated in the silver halide emulsion layer associated with the compound.

3. The color photographic material as set forth in claim 1 wherein said dye releasing redox compound is incorporated in a layer disposed adjacent to the silver halide emulsion layer associated with the compound.

4. The color photographic material as set forth in claim 1 wherein said dye releasing redox compound is selected from the group consisting of:

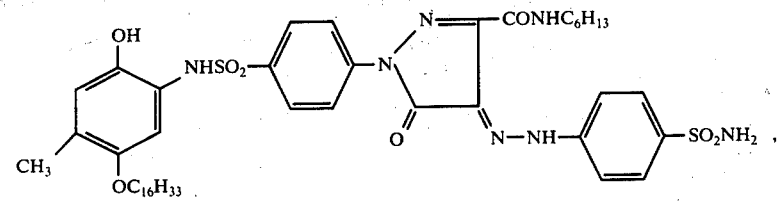

-continued
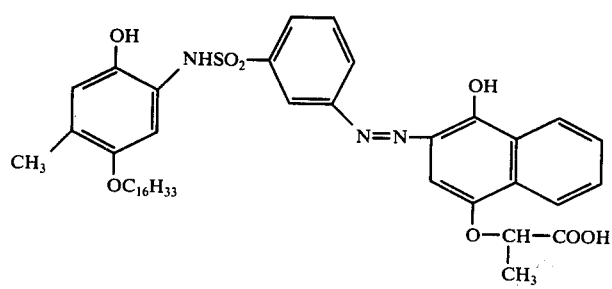
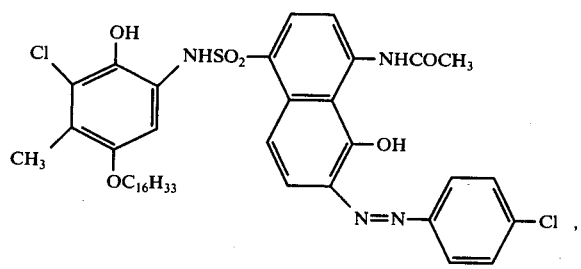
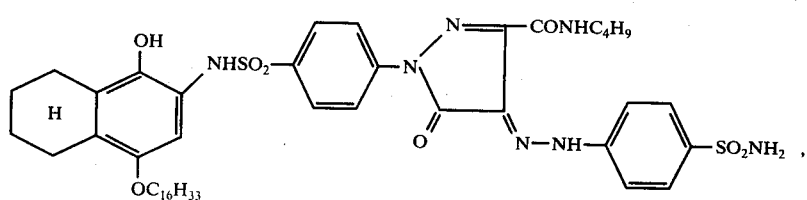
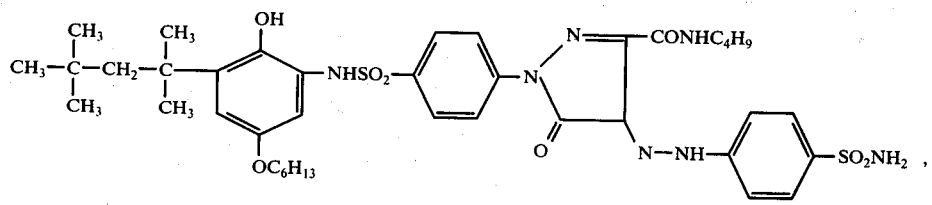
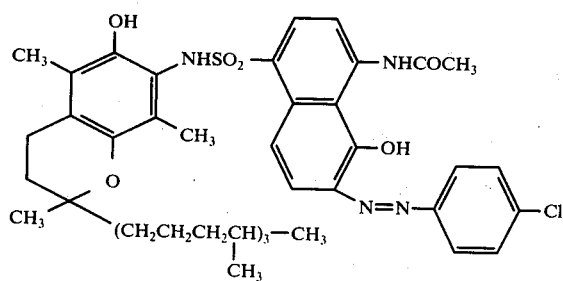
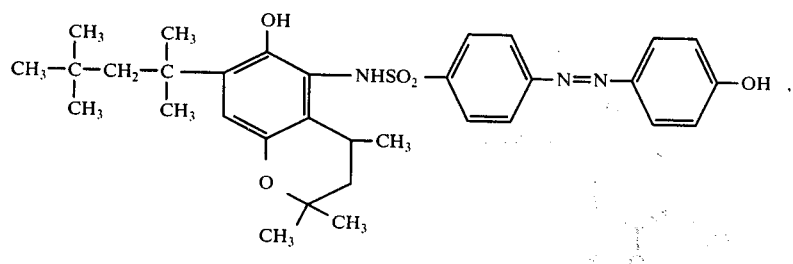

-continued
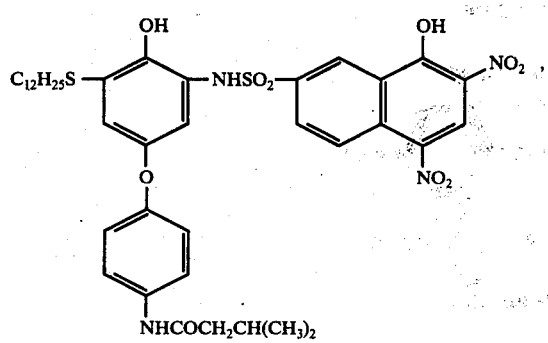
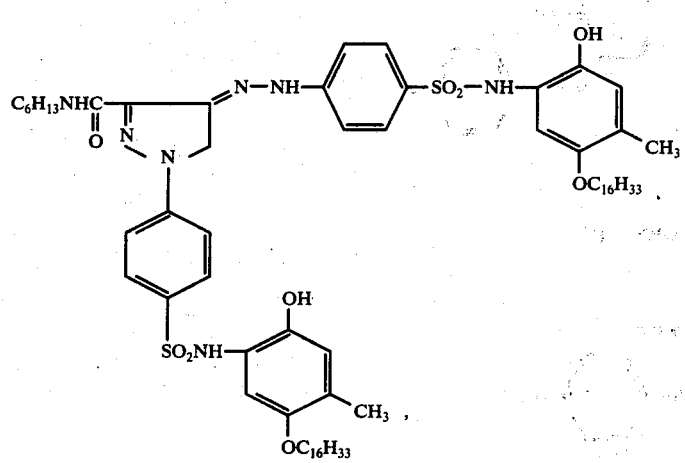
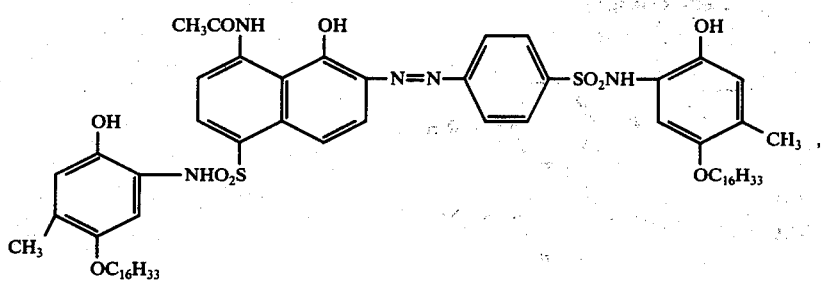
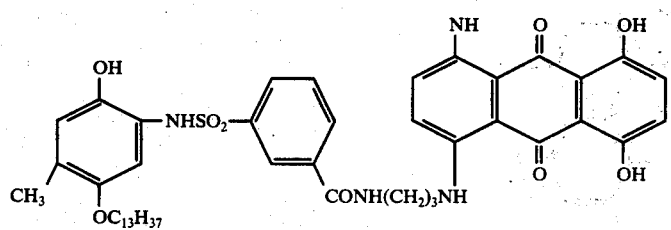
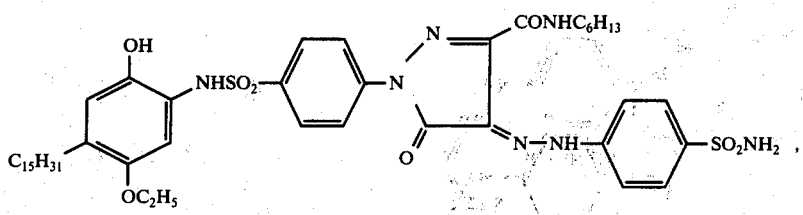

-continued
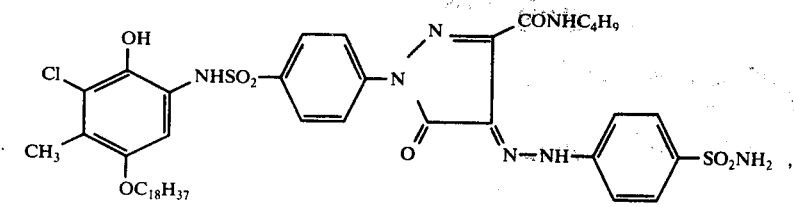
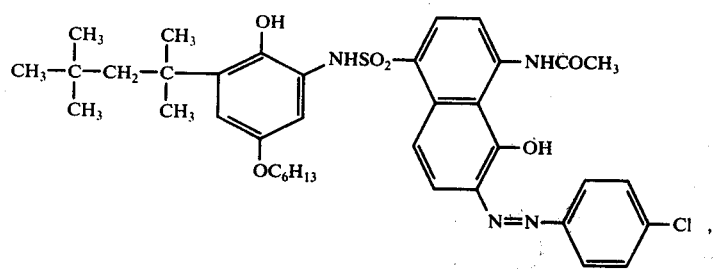
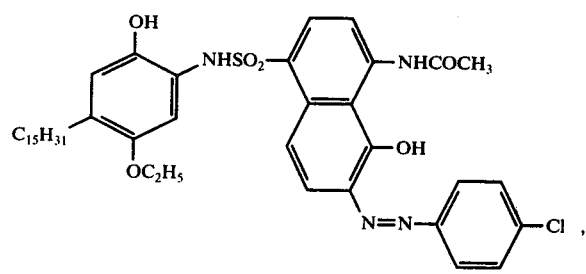
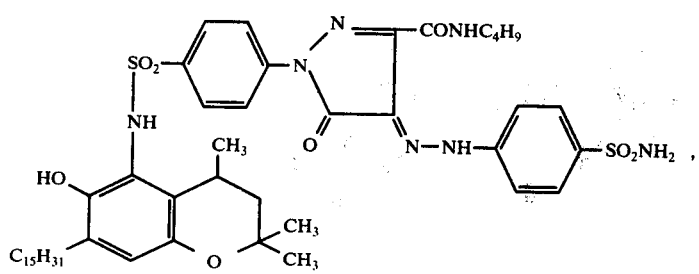
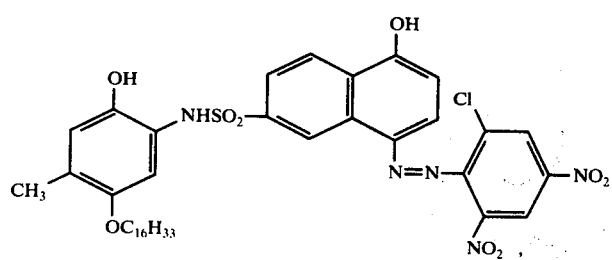
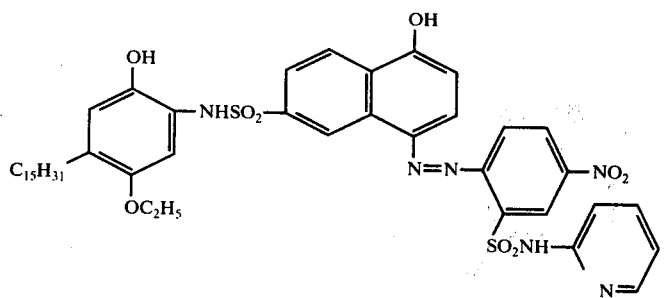

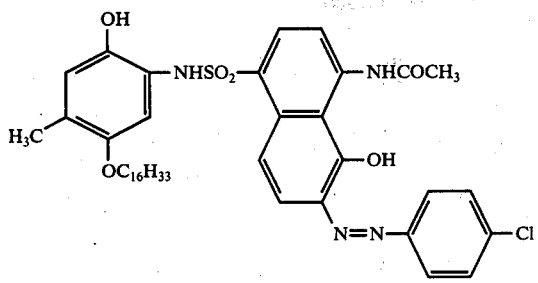

and

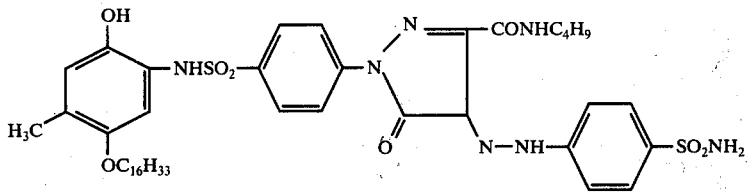

5. A photographic unit for a color diffusion transfer process comprising a support, a photosensitive element, an image-receiving element, and an aqueous and alkaline liquid processing composition, said photosensitive element comprising at least one silver halide emulsion layer having associated therewith a dye releasing redox compound represented by the general formula $$\underset{Xn}{\underset{OR}{\bigotimes}}\overset{G}{\underset{NHSO_2Col}{}}$$

wherein
G represents a hydroxyl group or a group giving a hydroxyl group upon hydrolysis,
Col represents a dye or a group giving a dye, both being diffusible when released upon hydrolysis;
R represents an alkyl group or an aromatic group,
X represents an electron donating group substituent when $n$ is 1, or substituents, which may be the same or different, one of said substituents being an electron donating group and the second or second and third substituents being selected from the group consisting of an electron donating group or a halogen atom, wherein X groups may form a condensed ring, excluding an aromatic ring, with each other or with OR,
$n$ is 1, 2 or 3 and the total carbon number of $X_n$ and R is larger than 8.

6. The photographic unit for a color diffusion transfer process as set forth in claim 5 wherein said dye releasing redox compound is incorporated in the at least one silver halide emulsion layer associated with the compond.

7. The photographic unit for a color diffusion transfer process as set forth in claim 5 wherein said dye releasing redox compound is incorporated in a layer disposed adjacent to the silver halide emulsion layer associated with the compound.

8. The photographic unit for a color diffusion transfer process as set forth in claim 5 wherein said photsensitive element has three silver halide emulsion layers each having associated therewith the dye releasing redox compound.

9. The photographic unit for color diffusion transfer process as set forth in claim 5 wherein said photosensitive element comprises a blue-sensitive silver halide emulsion layer having associated therewith a yellow dye releasing redox compound, a green-sensitive silver halide emulsion layer having associated therewith a magenta dye releasing redox compond, and a red sensitive silver halide emulsion layer having associated therewith a cyan dye releasing redox compound, said dye releasing redox compounds being within the general formula.

10. The photographic unit for a color diffusion transfer process as set forth in claim 5 wherein said dye releasing redox compound is selected from the group consisting of:

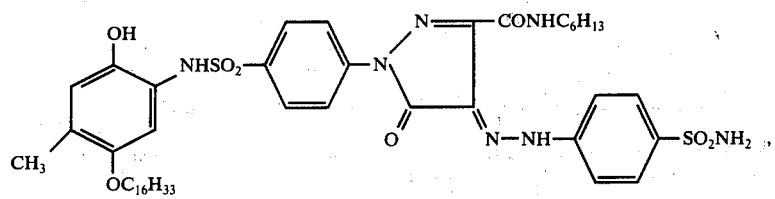

-continued
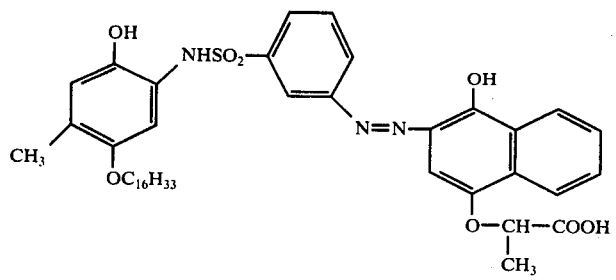
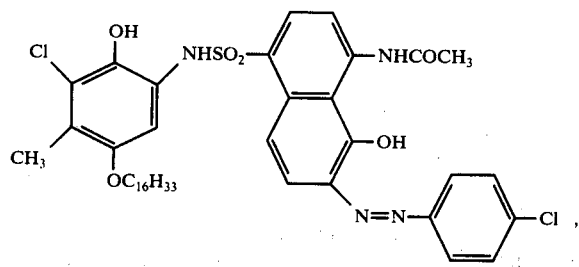
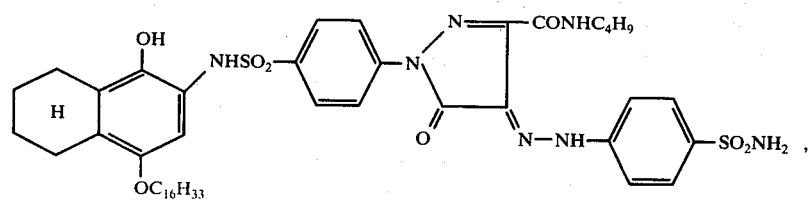
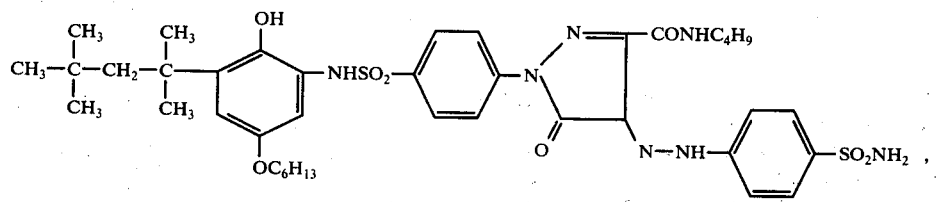
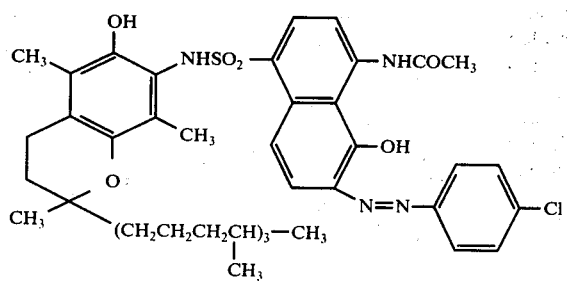
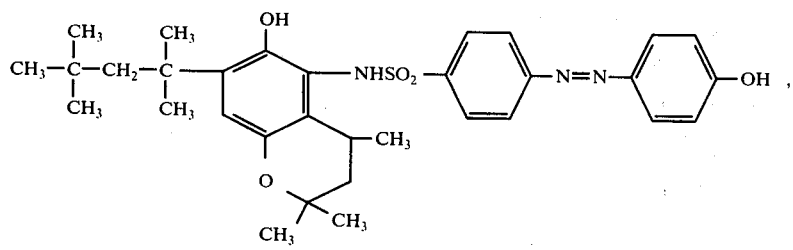

-continued
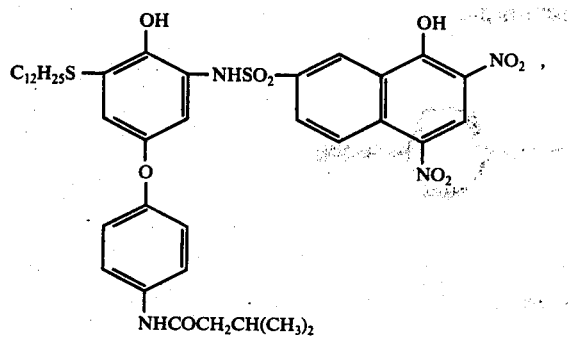
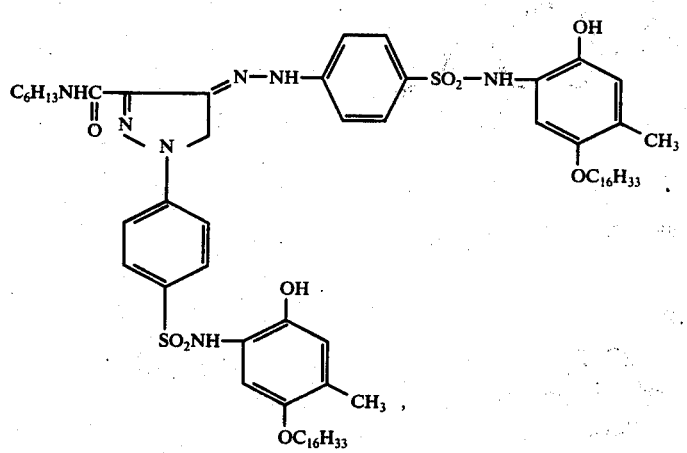
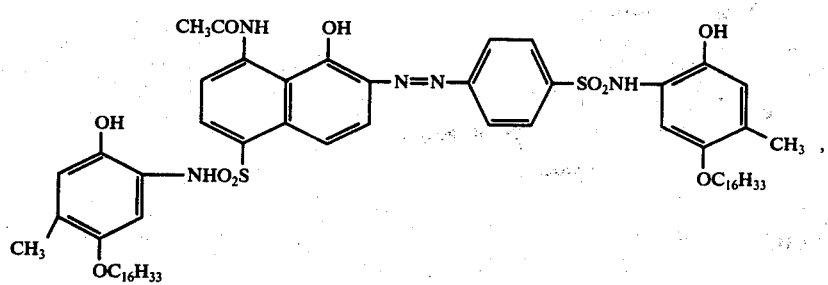
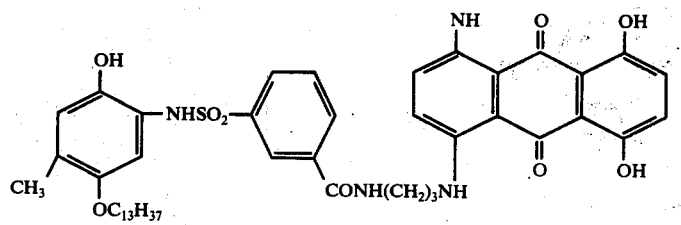
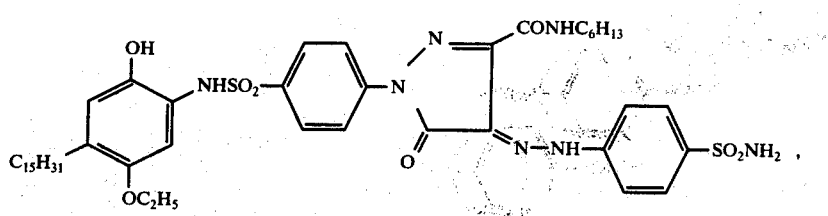

-continued
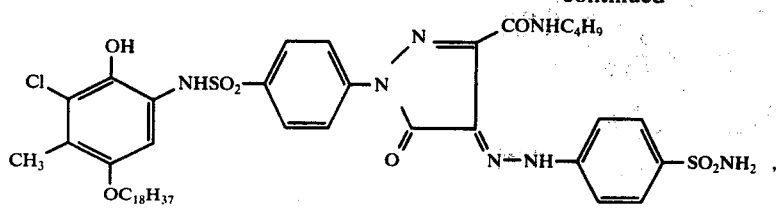
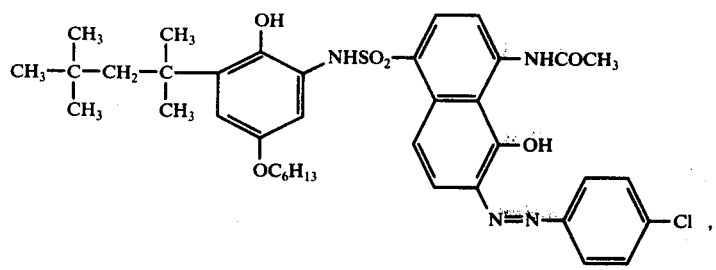
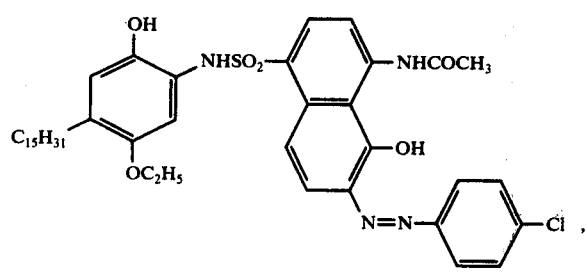
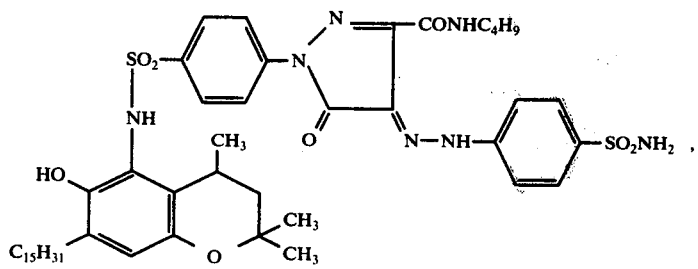
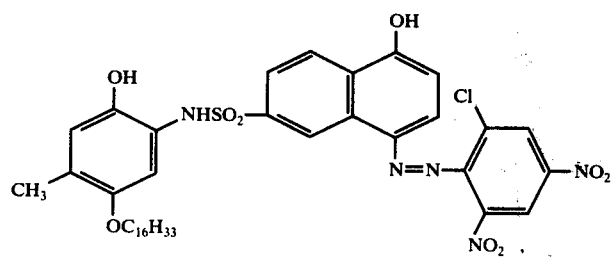
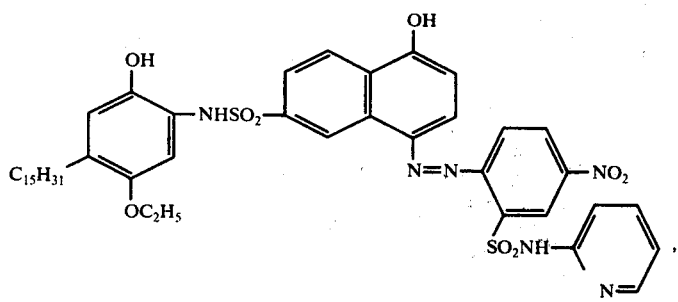

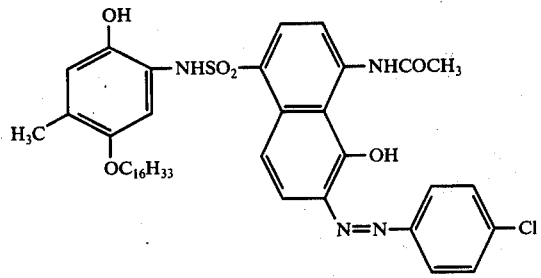

and

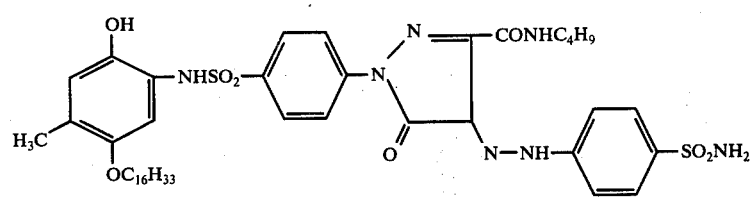

11. The photographic unit for a color diffusion transfer process as set forth in claim 5, wherein the photosensitive element is superimposed on the image receiving element which contains a transparent support having thereon a dyeable mordant layer, through a reflecting layer disposed between the mordant layer and the silver halide emulsion layer, the dye image transferred after exposure to the mordant layer being observed without stripping the photosensitive element.

12. The photographic unit for a color diffusion transfer process as set forth in claim 5, wherein the photosensitive element is superimposed on the image receiving element in a face-to-face relationship and the photographic unit, after image-wise exposure, is processable by spreading an alkaline processing solution between both elements.

13. The color photographic material as set forth in claim 1, wherein the group giving a hydroxyl group upon hydrolysis is an acyloxy group.

14. The color photographic material as set forth in claim 13, wherein the said acyloxy group is an acetoxy group, a benzoyloxy group, a p-nitrobenzoyloxy group, a methane sulfonyloxy group, a p-toluenesulfonyloxy group, or a propionyloxy group.

15. The color photographic material as set forth in claim 1, wherein the dye represented by Col is an azo dye, an azomethine dye, an indoaniline dye, an indophenol dye, a triphenylmethane dye, an anthraquinone dye, an indigo dye, or metal complex salts of these dyes.

16. The color photographic material as set forth in claim 1, wherein the said group which yields a dye by hydrolysis is an acylated auxochrome of the dye.

17. The color photographic material as set forth in claim 1, wherein the said dye or group giving a dye upon hydrolysis has a group capable of providing water solubility.

18. The color photographic material as set forth in claim 17, wherein the group capable of providing water solubility is a hydroxy group, a sulfonic acid or salts thereof, a sulfonamide group, or a carboxy group.

19. The color phogographic material as set forth in claim 1, wherein the alkyl group of R is a straight chain or branched chain alkyl group having 1 to 24 carbon atoms, which may be substituted.

20. The color photograhic material as set forth in claim 1, wherein the electron donating group of X is a straight or branched chain alkyl group, a straight or branched chain alkoxy group, an alkylthio group, an arylthio group, or an acylamino group.

21. The photographic unit for a color diffusion transfer process as set forth in claim 5, wherein the group giving a hydroxyl group upon hydrolysis is an acyloxy group.

22. The photographic unit for a color diffusion transfer process as set forth in claim 21, wherein the said acyloxy group is an acetoxy group, a benxoyloxy group, a p-nitro-benzoyloxy group, a methane sulfonyloxy group, a p-toluenesulfonyloxy group, or a propionyloxy group.

23. The photographic unit for a color diffusion transfer process as set forth in claim 5, wherein the dye represented by Col is an azo dye, an azomethine dye, an indoaniline dye, an indophenol dye, a triphenylmethane dye, an anthraquinone dye, an indigo dye, or metal complex salts of these dyes.

24. The photographic unit for a color diffusion transfer process as set forth in claim 5, wherein the said dye or group giving a dye upon hydrolysis has a group capable of providing water solublity.

25. The photographic unit for a color diffusion transfer process as set forth in claim 24, wherein the group capable of providing water solubility is a hydroxy group, a sulfonic acid or salts thereof, a sulfonamide group, or a carboxy group.

26. The photographic unit for a color diffusion transfer processes set forth in claim 5, wherein the alkyl group of R is a straight chain or branched chain alkyl group having 1 to 24 carbon atoms, which may be substituted.

27. The photographic unit for a color diffusion transfer process as set forth in claim 5, wherein the electron donating group of X is a straight or branched chain alkyl group, a straight or branched chain alkoxy group, an alkylthio group, an arylthio group, or an acylamino group.

28. The photographic unit for a color diffusion transfer process as set forth in claim 5, wherein the said group which yields a dye upon hydrolysis is an acylated auxochrome of the dye.

* * * * *